(12) United States Patent
van 't Klooster et al.

(10) Patent No.: US 9,284,311 B2
(45) Date of Patent: Mar. 15, 2016

(54) AMINOTRIAZOLOPYRIDINE FOR USE IN THE TREATMENT OF INFLAMMATION, AND PHARMACEUTICAL COMPOSITIONS THEREOF

(71) Applicants: Gerben Albert Eleutherius van 't Klooster, Mechelen (BE); Florence Sylvie Namour, Romainville (FR); Réginald Christophe Xavier Brys, Mechelen (BE); Luc Juliaan Corina van Rompaey, Mechelen (BE)

(72) Inventors: Gerben Albert Eleutherius van 't Klooster, Mechelen (BE); Florence Sylvie Namour, Romainville (FR); Réginald Christophe Xavier Brys, Mechelen (BE); Luc Juliaan Corina van Rompaey, Mechelen (BE)

(73) Assignee: GALAPAGOS NV, Mechelen (BE)

( * ) Notice: Subject to any disclaimer, the term of this patent is extended or adjusted under 35 U.S.C. 154(b) by 133 days.

(21) Appl. No.: 13/913,597

(22) Filed: Jun. 10, 2013

(65) Prior Publication Data
US 2013/0345209 A1    Dec. 26, 2013

Related U.S. Application Data

(60) Provisional application No. 61/663,520, filed on Jun. 22, 2012.

(51) Int. Cl.
| | | |
|---|---|---|
| A61K 31/407 | (2006.01) | |
| A61K 31/44 | (2006.01) | |
| C07D 471/04 | (2006.01) | |
| A61K 31/541 | (2006.01) | |
| A61K 45/06 | (2006.01) | |

(52) U.S. Cl.
CPC ............ C07D 471/04 (2013.01); A61K 31/541 (2013.01); A61K 45/06 (2013.01)

(58) Field of Classification Search
None
See application file for complete search history.

(56) References Cited

U.S. PATENT DOCUMENTS

2010/0093698 A1*  4/2010  Bahmanyar .......... C07D 519/00
                                                514/210.21

FOREIGN PATENT DOCUMENTS

WO    WO2010141796    12/2010
WO    WO2010149769    12/2010

OTHER PUBLICATIONS

Sikora, Current Science 2001, 81(5), 549-554.*
Zips et al., In vivo, 2005, 19, 1-8.*

Argiles, et al., Curr Opin Clin Nutr Metab Care, "Catabolic proinflammatory cytokines," 1998; 1: 245-51.
Bush, et al., Arthritis & Rheumatism, "Reduction of Joint Inflammation and Bone Erosion in Rat Adjuvant Arthritis by Treatment With Interleukin-17 Receptor IgG1 Fc Fusion Protein," 2002; 46(3): 802-805.
Firestein, Nature, "Evolving concepts of rheumatoid arthritis," 2003; 423: 356-361.
Geron, et al., Cancer Cell, "Selective Inhibition of JAK2-Driven Erythroid Differentiation of Polycythemia Vera Progenitors," 2008; 13: 321-330.
Ip, et al., British Society for Immunology, Clinical and Experimental Immunology, "Interleukin (IL)-4 and IL-13 up-regulate monocyte chemoattractant protein-1 expression in human bronchial epithelial cells: involvement of p38 mitogen-activated protein kinase, extracellular signal-regulated kinase 1/2 and Janus kinase-2 but not c-Jun NH2-terminal kinase 1/2 signalling pathways," 2006; 145: 162-172.
Jou, et al., Arthritis & Rheumatism, "Thrombospondin 1 as an Effective Gene Therapeutic Strategy in Collagen-Induced Arthritis," 2005; 52(1): 339-344.
Khachigian, et al., Protocol, "Collagen antibody-induced arthritis," 2006; 1(5): 2512-2516.
Kopf, et al., Nature Reviews, Drug Discovery, "Averting inflammation by targeting the cytokine environment," 2010; 9: 703-718.

(Continued)

*Primary Examiner* — Svetlana M Ivanova
(74) *Attorney, Agent, or Firm* — Klauber & Jackson LLC

(57) ABSTRACT

The present invention relates to the compound according to Formula I, and to its use in medicine, in particular in the treatment of inflammatory conditions, autoimmune diseases, proliferative diseases, allergy, transplant rejection, diseases involving impairment of cartilage turnover, congenital cartilage malformations, and/or diseases associated with hypersecretion of IL6 or interferons. In particular, the compound inhibits JAK a family of tyrosine kinases, and more particularly JAK1. The present invention also provides pharmaceutical compositions comprising the compound, methods for the prophylaxis and/or treatment of diseases involving inflammatory conditions, autoimmune diseases, proliferative diseases, allergy, transplant rejection, diseases involving impairment of cartilage turnover, congenital cartilage malformations, and/or diseases associated with hypersecretion of IL6 or interferons by administering the compound.

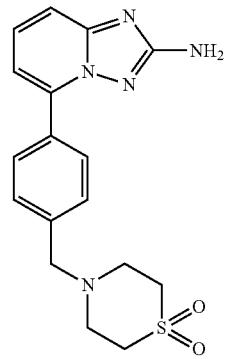

6 Claims, 6 Drawing Sheets

(56) References Cited

OTHER PUBLICATIONS

Kudlacz, et al., European Journal of Pharmacology, "The JAK-3 inhibitor CP-690550 is a potent anti-inflammatory agent in a murine model of pulmonary eosinophilia," 2008; 582: 154-161.
Lin, et al., British Journal of Pharmacology, "Anti-rheumatic activities of histone deacetylase (HDAS) inhibitors in vivo in collagen-inducedarthritis in rodents," 2007; 150: 862-872.
McGinnity, et al., Drug Metabolism and Disposition, "Evaluation of Fresh and Cryopreserved Hepatocytes as in Vitro Drug Metabolism Tools for the Prediction of Metabolic Clearance," 2004; 32(11): 1247-1253.
Mullighan, et al., PNAS, "JAK mutations in high-risk childhood acute lymphoblastic leukemia," 2009; 106(23): 9414-18.
Nials, et al., Disease Models and Mechanisms, "Mouse models of allergic asthma: acute and chronic allergen challenge," 2008; 1: 213-220.
Nishida, et al., Arthritis Rheum., "Histone Deacetylase Inhibitor Suppression of Autoantibody-Mediated Arthritis in Mice via Regulation of p16INK4a and p21WAF1/Cip1 Expression," 2004; 50(10): 3365-3376.
O'Sullivan, et al., Molecular Immunology, "Cytokine receptor signaling through the Jak-Stat-Socs pathway in disease," 2007; 44: 2497-2506.
Pernis, et al., J. Clin. Invest., "JAK-STAT signaling in asthma," 2002; 109: 1279-1283.
Salvemini, et al., Arthritis & Rheumatism, "Amelioration of Joint Disease in a Rat Model of Collagen-Induced Arthritis by M40403, a Superoxide Dismutase Mimetic," 2001; 44(12): 2909-2921.
Shelton, et al., Pain, "Nerve growth factor mediates hyperalgesia and cachexia in auto-immune arthritis," 2005; 116: 8-16.
Sims, et al., "Targeting Osteoclasts With Zoledronic Acid Prevents Bone Destruction in Collagen-Induced Arthritis," 2004; 50(7): 2338-2346.
Vainchenker, et al., Seminars in Cell & Developmental Biology, "JAKs in pathology: Role of Janus kinases in hematopoietic malignancies and immunodeficiencies," 2008; 19: 385-393.
Walsmith, et al., J Rheumatol, "Tumor Necrosis Factor-ί Production Is Associated with Less Body Cell Mass in Women with Rheumatoid Arthritis," 2004; 31: 23-9.
Wernig, et al., Cancer Cell, "Efficacy of TG101348, a Selective JAK2 Inhibitor, in Treatment of a Murine Model of JAK2V617F-Induced Polycythemia Vera," 2008; 13: 311-320.
Wirtz, et al., Advanced Drug Delivery Reviews, Mouse models of inflammatory bowel disease,: 2007; 59: 1073-1083.
Xiang, et al., Blood, "Identification of somatic JAK1 mutations in patients with acute myeloid leukemia," 2008; 111: 4809-4812.
Rall, et al., Rheumatology, "Rheumatoid cachexia: metabolic abnormalities, mechanisms and interventions," 2004; 43: 1219-1223.
Zikherman, et al., J Clin Invest., "Unraveling the functional implications of GWAS: how T cell protein tyrosine phosphatase drives autoimmune disease," 2011; 121(12): 4618-4621.
Zenz, et al., Nature, "Psoriasis-like skin disease and arthritis caused by inducible epidermal deletion of Jun proteins," 2005; 437: 369-375.
Dolgin, Nature Reviews Drug Discovery, "Companies hope for kinase inhibitor JAKpot," 2011; 10: 717-718.
Punwani, et al., J Am Acad Dermatol., "Preliminary clinical activity of a topical JAK1/2 inhibitor in the treatment of psoriasis," 2012; 67(4): 658-64.
Ingersoll, et al., J Behav Med., "The impact of medication regimen factors on adherence to chronic treatment: a review of literature," 2008; 31(3): 213-224.
EMAE, Committee for Medicinal Products for Human Use (CHMP), Guideline on Clinical Investigation of Medicinal Products Indicated for the Treatment of Psoriasis, London, Nov. 18, 2004.
Verstovsek, Hematology Am Soc Hematol Educ Program, "Therapeutic potential of JAK2 inhibitors," 2009; 636-42.
Zhang, et al., Proc Natl Acad Sci USA, "Activation of Jak/STAT proteins involved in signal transduction pathway mediated by receptor for interleukin 2 in malignant T lymphocytes derived from cutaneous anaplastic large T-cell lymphoma and Sezary syndrome," 1996; 93: 9148-9153.
Berishaj, et al., Breast Cancer Res., "Stat3 is tyrosine-phosphorylated through the interleukin-6/glycoprotein 130/Janus kinase pathway in breast cancer," 2007; 9(3): R32.
Saharinen, et al., Molecular and Cellular Biology, "Regulation of the Jak2 Tyrosine Kinase by Its Pseudokinase Domain," 2000; 20(10): 3387-3395.
Choy, et al., N Engl J Med., "Cytokine Pathways and Joint Inflammation in Rheumatoid Arthritis," 2001; 344(12): 907-916.
Lee, et al., The Lancet, "Rheumatoid arthritis," 2001; 358: 903-911.
O'Dell, et al., N Engl J Med., "Therapeutic strategies for rheumatoid arthritis," 2004; 350: 2591-602.
Smolen, et al., Nat Rev Drug Discov., "Therapeutic strategies for rheumatoid arthritis," 2003; 2(6): 473-88.
Tam, et al., British Journal of Cancer, "Expression levels of the JAK/STAT pathway in the transition from hormone-sensitive to hormone-refractory prostate cancer," 2007; 97: 378-383.
Constantinescu, et al., Trends in Biochemical Sciences, "Mining for JAK-STAT mutations in cancer," 2007; 33(3): 122-131.
Tetsuji, et al., Arthritis Res., "The paradigm of IL-6: from basic science to medicine," 2002; 4 (suppl 3): S233-S242.
Bundgard, Adv Drug Del Rev., "Prodrugs as a means to improve the delivery of peptide drugs," 1992; 8: 1-38.
Oste, et al., ECTC Montreal 2007: A high throughput method of measuring bone architectural disturbance in a murine CIA model by micro-CT morphometry.

\* cited by examiner

AMINOTRIAZOLOPYRIDINE FOR USE IN THE TREATMENT OF INFLAMMATION, AND PHARMACEUTICAL COMPOSITIONS THEREOF

CROSS REFERENCE TO RELATED APPLICATION

The present application claims the priority of provisional application U.S. Ser. No. 61/663,520 filed on Jun. 22, 2012, and the disclosure of said application is incorporated by reference herein in its entirety. Applicants claim the benefits of said application under 35 U.S.C. §119(e).

FIELD OF THE INVENTION

The present invention relates to the medical use of a compound of the invention according to Formula I. In particular the present invention relates to the use of a compound of the invention according to Formula I for the treatment of inflammatory conditions, autoimmune diseases, proliferative diseases, allergy, transplant rejection, diseases involving impairment of cartilage turnover, congenital cartilage malformations, and/or diseases associated with hypersecretion of IL6 or interferons. In particular, the compound inhibits JAK, a family of tyrosine kinases, and more particularly JAK1. The present invention also provides pharmaceutical compositions comprising the compound and methods for the prophylaxis and/or treatment of diseases including inflammatory conditions, autoimmune diseases, proliferative diseases, allergy, transplant rejection, diseases involving impairment of cartilage turnover, congenital cartilage malformations, and/or diseases associated with hypersecretion of IL6 or interferons by administering a compound of the invention according to Formula I.

Janus kinases (JAKs) are cytoplasmic tyrosine kinases that transduce cytokine signaling from membrane receptors to STAT transcription factors. Four JAK family members are described, JAK1, JAK2, JAK3 and TYK2. Upon binding of the cytokine to its receptor, JAK family members auto- and/or transphosphorylate each other, followed by phosphorylation of STATs that then migrate to the nucleus to modulate transcription. JAK-STAT intracellular signal transduction serves the interferons, most interleukins, as well as a variety of cytokines and endocrine factors such as EPO, TPO, GH, OSM, LIF, CNTF, GM-CSF and PRL (Vainchenker W. et al. (2008)).

The combination of genetic models and small molecule JAK inhibitor research revealed the therapeutic potential of several JAKs.

JAK1 is a target in the immuno-inflammatory disease area. JAK1 heterodimerizes with the other JAKs to transduce cytokine-driven pro-inflammatory signaling. Therefore, inhibition of JAK1 is of interest for immuno-inflammatory diseases with pathology-associated cytokines that use JAK1 signaling, such as IL-6, IL-4, IL-5, IL-12, IL-13, IL-23, or IFNgamma, as well as for other diseases driven by JAK-mediated signal transduction.

In the JAK family members' roles, some overlap exists, since most signaling pathways involve more than one JAK, however for some growth factors such as erythropoietin and thrombopoietin, only JAK2 is involved.

JAK3 plays a major role in blocking immune function via transmission of signals generated by interleukin (IL)-2.

On the other hand, TYK2 would appear to work in combination with JAK2 and JAK3 in order to transduce signaling of cytokines such as IL-12 and IL-23.

The role of JAK enzymes has been mostly studied using mice where each of the JAK family members has been deleted. JAK1 knockout mice exhibit a perinatal lethal phenotype and also have defective lymphoid development and function as a result of defective signaling by cytokines through JAK1. JAK2 deficiency results in embryonic lethality at day 12 as a result of a failure in definitive erythropoiesis. JAK3-deficient mice have severe combined immunodeficiency (SCID) phenotype but do not have non-immune defects. (Verstovsek, 2009, Hematology Am Soc Hematol Educ Program., 636-42).

As has been observed with pan JAK inhibitors, non selective inhibition may be linked to side effects such as anemia, an increased rate of infections, lower neutrophil and lymphocyte counts, a decrease in haemoglobin, and elevated cholesterol levels, (Elie Dolgin, 2011, Nature Reviews Drug Discovery 10, 717-718).

Therefore, the development of a selective JAK inhibitor would be beneficial in order to minimize such side effects.

BACKGROUND OF THE INVENTION

The degeneration of cartilage is the hallmark of various diseases, among which rheumatoid arthritis and osteoarthritis are the most prominent. Rheumatoid arthritis (RA) is a chronic joint degenerative disease, characterized by inflammation and destruction of the joint structures. When the disease is unchecked, it leads to substantial disability and pain due to loss of joint functionality and even premature death. The aim of a RA therapy, therefore, is not only to slow down the disease but to attain remission in order to stop the joint destruction. Besides the severity of the disease outcome, the high prevalence of RA (~0.8% of adults are affected worldwide) means a high socio-economic impact. (For reviews on RA, we refer to Smolen and Steiner (2003); Lee and Weinblatt (2001); Choy and Panayi (2001); O'Dell (2004) and Firestein (2003)).

JAK1 is implicated in intracellular signal transduction for many cytokines and hormones. Pathologies associated with any of these cytokines and hormones can be ameliorated by JAK1 inhibitors. Hence, several allergy, inflammation and autoimmune disorders might benefit from treatment with compounds described in this invention including rheumatoid arthritis, systemic lupus erythematosus, juvenile idiopathic arthritis, osteoarthritis, asthma, chronic obstructive pulmonary disease (COPD), tissue fibrosis, eosinophilic inflammation, eosophagitis, inflammatory bowel diseases (e.g. Crohn's disease, ulcerative colitis), transplant, graft-versus-host disease, psoriasis, myositis, psoriatic arthritis, ankylosing spondylitis, juvenile idiopathic arthritis, and multiple sclerosis (Kopf et al., 2010).

Psoriasis is a disease that can affect the skin. The cause of psoriasis is not fully understood, however, it is believed that it is an immune mediated related disease linked to the release of cytokines, in particular TNFα, which causes inflammation and rapid reproduction of the skin cells. This hypothesis has been corroborated by the observation that immunosuppressant medication can clear psoriasis plaques (Zenz R, Eferl R, Kenner L, et al. (2005). "Psoriasis-like skin disease and arthritis caused by inducible epidermal deletion of Jun proteins". Nature 437 (7057): 369-75)

Psoriasis can also cause inflammation of the joints, which is known as psoriatic arthritis. Between 10-30% of all people with psoriasis also have psoriatic arthritis (Committee for Medicinal Products for Human Use (CHMP) (18 Nov. 2004). "Guideline on Clinical Investigation of Medicinal Products indicated for the treatment of Psoriasis"). Because of its chronic recurrent nature, psoriasis is a challenge to treat. It has recently been demonstrated that inhibition of JAK could result in successful improvement of the psoriatic condition. (Punwani et al., (2012) "Preliminary clinical activity of a topical JAK1/2 inhibitor in the treatment of psoriasis" J Am Acad Dermatol., 67, 4, 658-664).

Inflammatory bowel disease (IBD) is a group of inflammatory conditions of the colon and small intestine. The major types of IBD are Crohn's disease and ulcerative colitis. Recently, it has been found via genome-wide association (GWAS) studies that T cell protein tyrosine phosphatase (TCPTP) is a JAK/STAT and growth factor receptor phosphatase that has been linked to the pathogenesis of type 1 diabetes, rheumatoid arthritis, and Crohn's disease by GWAS (Zikherman et al., J Clin Invest. 2011 December; 121(12): 4618-21). Therefore, inhibition of the JAK pathway might provide a way of treating IBD.

JAK family members have been implicated in additional conditions including myeloproliferative disorders (O'Sullivan et al, 2007, Mol Immunol 44(10):2497-506), where mutations in JAK2 have been identified. This indicates that inhibitors of JAK in particular JAK2 may also be of use in the treatment of myeloproliferative disorders. Additionally, the JAK family, in particular JAK1, JAK2 and JAK3, has been linked to cancers, in particular leukaemias e.g. acute myeloid leukaemia (O'Sullivan et al, 2007, Mol. Immunol. 44(10):2497-506; Xiang et al., 2008, "Identification of somatic JAK1 mutations in patients with acute myeloid leukemia" Blood First Edition Paper, prepublished online Dec. 26, 2007; DOI 10.1182/blood-2007-05-090308) and acute lymphoblastic leukaemia (Mullighan et al, 2009)), cutaneous T-cell lymphoma (Zhang et al., 1996, PNAS, 93, 9148-9153) or solid tumours e.g. uterine leiomyosarcoma (Constantinescu et al., 2007, Trends in Biochemical Sciences 33(3): 122-131), prostate cancer (Tam et al., 2007, British Journal of Cancer, 97, 378-383) and breast cancer (Berishaj et al., 2007, Breast Cancer Research 9: R32). These results indicate that inhibitors of JAK, in particular of JAK1, may also have utility in the treatment of cancers (leukaemias and solid tumours e.g. uterine leiomyosarcoma, prostate cancer).

In addition, Castleman's disease, multiple myeloma, mesangial proliferative glomerulonephritis, psoriasis, and Kaposi's sarcoma are likely due to hypersecretion of the cytokine IL-6, whose biological effects are mediated by intracellular JAK-STAT signaling (Tetsuji Naka, Norihiro Nishimoto and Tadamitsu Kishimoto, Arthritis Res 2002, 4 (suppl 3):S233-S242). This result shows that inhibitors of JAK, may also find utility in the treatment of said diseases.

The current therapies are not satisfactory and therefore there remains a need to identify further compounds that may be of use in the treatment of inflammatory conditions, autoimmune diseases, proliferative diseases, allergy, transplant rejection, diseases involving impairment of cartilage turnover, congenital cartilage malformations, and/or diseases associated with hypersecretion of IL6 or interferons, in particular rheumatoid arthritis.

Additionally, these conditions are chronic conditions which require long term therapy, and repeated intake of the drug. Long term treatment might be a heavy burden on the patient and the practitioner alike, since the patient might be or become intolerant to the drug, and furthermore high dosage, or high dosage frequency may result in uncomfortable side effects, and/or low patient compliance, where the patient may occasionally, deliberately or accidentally, miss a dose. The impact of non-adherence varies across chronic illnesses, and ranges from minimal to very significant. (Ingersoll et al., 2008 J Behav Med.; 31(3): 213-224).

Therefore, there is a need to identify more compounds to reinforce the arsenal of the practitioner, and compounds with low frequency dosage regimen to improve the life of the patients.

In the quest to discover new medicines, criteria are often set to identify the best suitable candidate, thus many compounds are rapidly assessed in an in vitro model, and equally rapidly discarded if they do not meet said criteria. In vitro studies usually have a higher throughput than in vivo studies and greatly help with the decision making process. Thus the in vitro model is usually expected to be predictive of the in vivo behavior of the drug, and compounds which prima facie would not appear to offer a suitable profile in vitro are discarded. In this context, the compound according to Formula I when investigated showed in vitro profile of low interest, however, in vivo studies revealed unexpected properties in humans specifically.

SUMMARY OF THE INVENTION

The present invention is based on the discovery that the compound of the invention according to Formula I may be useful as a medicament. In a particular aspect, the compound of the invention according to Formula I is an inhibitor of JAK, and more particularly JAK1.

The present invention also provides methods for the production of the compound of the invention according to Formula I, pharmaceutical compositions comprising the compound of the invention according to Formula I and methods for the prophylaxis and/or treatment of inflammatory conditions, autoimmune diseases, proliferative diseases, allergy, transplant rejection, diseases involving impairment of cartilage turnover, congenital cartilage malformations, and/or diseases associated with hypersecretion of IL6 or interferons, in particular rheumatoid arthritis, by administering the compound of the invention according to Formula I.

Accordingly, in a first aspect of the invention, a compound of the invention is provided for use in medicine having a Formula I:

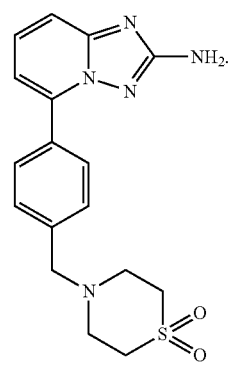

I

In another embodiment, the compound of the invention may be prepared in a therapeutic combination, with a further therapeutically active ingredient. The further therapeutically active ingredient may be a compound for the treatment of the same conditions and diseases outlined herein with respect to the compound of formula I. In a particular embodiment, the further therapeutically active ingredient may be a compound for the treatment of arthritis. In a most particular aspect, the further therapeutically active ingredient is a compound for the treatment of rheumatoid arthritis.

The compound of the invention according to Formula I, surprisingly, exhibits in vivo in human a very different profile from other animal species, which contrasts with in vitro predictions. Indeed, in vivo it has been demonstrated that in human, the apparent terminal half life of the compound of the invention according to Formula I is significantly longer than in the other animal species by at least 3 fold. This causes accumulation in human resulting in a maintained therapeutic effect over an extended period of time, thereby allowing once daily to once weekly dosing. Thus the compound of the invention according to Formula I may provide advantages including a low frequency dosage regimen and/or increased patient compliance. In particular, the impact of non adherence, if the patient misses a dose, might be reduced.

In a particular aspect, the compound of the invention according to Formula I is provided that may be used in a method for the prophylaxis and/or treatment of inflammatory conditions, autoimmune diseases, proliferative diseases, allergy, transplant rejection, diseases involving impairment of cartilage turnover, congenital cartilage malformations, and/or diseases associated with hypersecretion of IL6 or interferons, in particular rheumatoid arthritis.

In a further aspect, the present invention provides pharmaceutical compositions comprising the compound of the invention according to Formula I, and a pharmaceutical carrier, excipient or diluent. In a particular aspect, the pharmaceutical composition may additionally comprise further therapeutically active ingredients suitable for use in combination with the compound of the invention according to Formula I. In a more particular aspect, the further therapeutically active ingredient is a compound for the treatment of arthritis. In a most particular aspect, the further therapeutically active ingredient is a compound for the treatment of rheumatoid arthritis.

Moreover, the compound of the invention according to Formula I, useful in the pharmaceutical compositions and treatment methods disclosed herein, is pharmaceutically acceptable as prepared and used.

In a further aspect of the invention, this invention provides a method of treating a mammal, in particular humans, susceptible to or afflicted with a condition selected from among those listed herein, and particularly inflammatory conditions, autoimmune diseases, proliferative diseases, allergy, transplant rejection, diseases involving impairment of cartilage turnover, congenital cartilage malformations, and/or diseases associated with hypersecretion of IL6 or interferons, more particularly rheumatoid arthritis, which method comprises administering a therapeutically effective amount of the pharmaceutical composition or compound of the invention according to Formula I as described herein.

The present invention also provides pharmaceutical compositions comprising the compound of the invention according to Formula I, and a suitable pharmaceutical carrier, excipient or diluent. In a particular aspect, the pharmaceutical composition is for use in the prophylaxis and/or treatment of inflammatory conditions, autoimmune diseases, proliferative diseases, allergy, transplant rejection, diseases involving impairment of cartilage turnover, congenital cartilage malformations, and/or diseases associated with hypersecretion of IL6 or interferons, in particular rheumatoid arthritis.

In additional aspects, this invention provides methods for synthesizing the compound of the invention of according to Formula I, with representative synthetic protocols and pathways disclosed later on herein.

Other objects and advantages will become apparent to those skilled in the art from a consideration of the ensuing detailed description, including the following illustrative drawings.

DETAILED DESCRIPTION OF THE INVENTION

Definitions

Figure 1:
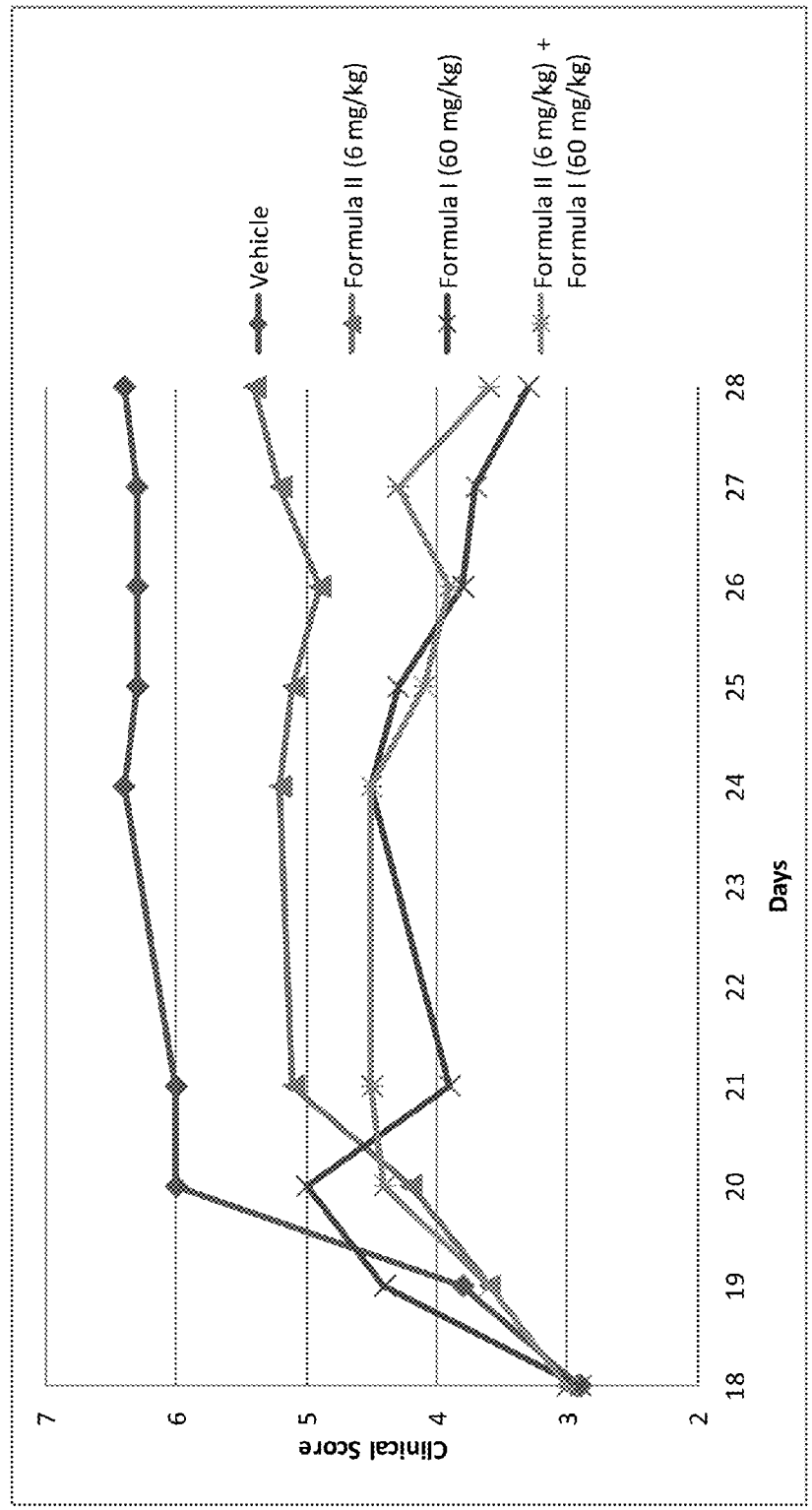
FIG. 1: Shows the rat CIA Clinical Score after treatment with the compounds disclosed herein.

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term 'substituted' is to be defined as set out below. It should be further understood that the terms 'groups' and 'radicals' can be considered interchangeable when used herein.

The articles 'a' and 'an' may be used herein to refer to one or to more than one (i.e. at least one) of the grammatical objects of the article. By way of example "an analogue" means one analogue or more than one analogue.

As used herein the term 'JAK' relates to the family of Janus kinases (JAKs) which are cytoplasmic tyrosine kinases that transduce cytokine signaling from membrane receptors to STAT transcription factors. Four JAK family members are described, JAK1, JAK2, JAK3 and TYK2 and the term JAK may refer to all the JAK family members collectively or one or more of the JAK family members as the context indicates.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of the compound according to Formula I that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term 'pharmaceutically acceptable cation' refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which the compound according to Formula I is administered.

'Solvate' refers to forms of the compound that are associated with a solvent, usually by a solvolysis reaction. This physical association includes hydrogen bonding. Conventional solvents include water, ethanol, acetic acid and the like. The compound according to Formula I may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Therapeutically effective amount' means the amount of a compound that, when administered to a subject for treating a disease, is sufficient to effect such treatment for the disease. The 'therapeutically effective amount' can vary depending on the compound, the disease and its severity, and the age, weight, etc., of the subject to be treated.

'Preventing' or 'prevention' refers to a reduction in risk of acquiring or developing a disease or disorder (i.e., causing at least one of the clinical symptoms of the disease not to develop in a subject that may be exposed to a disease-causing agent, or predisposed to the disease in advance of disease onset).

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, 'treating' or 'treatment' relates to slowing the progression of the disease.

As used herein the term 'inflammatory condition(s)' refers to the group of conditions including, rheumatoid arthritis, osteoarthritis, juvenile idiopathic arthritis, psoriasis, psoriatic arthritis, allergic airway disease (e.g. asthma, rhinitis), inflammatory bowel diseases (e.g. Crohn's disease, ulcerative colitis), endotoxin-driven disease states (e.g. complications after bypass surgery or chronic endotoxin states contributing to e.g. chronic cardiac failure), and related diseases involving cartilage, such as that of the joints. Particularly the term refers to rheumatoid arthritis, osteoarthritis, allergic airway disease (e.g. asthma) and inflammatory bowel diseases.

As used herein the term 'autoimmune disease(s)' refers to the group of diseases including obstructive airways disease, including conditions such as COPD, asthma (e.g. intrinsic asthma, extrinsic asthma, dust asthma, or infantile asthma) particularly chronic or inveterate asthma (for example late asthma and airway hyperreponsiveness), bronchitis (including bronchial asthma), systemic lupus erythematosus (SLE), cutaneous lupus erythematosus (CLE), multiple sclerosis, type I diabetes mellitus and complications associated therewith, atopic eczema (atopic dermatitis), contact dermatitis and further eczematous dermatitis, inflammatory bowel disease (e.g. Crohn's disease or ulcerative colitis), atherosclerosis and amyotrophic lateral sclerosis. Particularly the term refers to COPD, asthma, type I diabetes mellitus and inflammatory bowel disease.

As used herein the term 'proliferative disease(s)' refers to conditions such as cancer (e.g. uterine leiomyosarcoma or prostate cancer), myeloproliferative disorders (e.g. polycythemia vera, essential thrombocytosis and myelofibrosis), leukemia (e.g. acute myeloid leukaemia and acute lymphoblastic leukemia), multiple myeloma, psoriasis, restenosis, sclerodermitis or fibrosis. In particular the term refers to cancer, leukemia, multiple myeloma and psoriasis.

As used herein, the term 'cancer' refers to a malignant or benign growth of cells in skin or in body organs, for example but without limitation, breast, prostate, lung, kidney, pancreas, stomach or bowel. A cancer tends to infiltrate into adjacent tissue and spread (metastasise) to distant organs, for example to bone, liver, lung or the brain. As used herein the term cancer includes both metastatic tumour cell types, such as but not limited to, melanoma, lymphoma, leukaemia, fibrosarcoma, rhabdomyosarcoma, and mastocytoma and types of tissue carcinoma, such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer, ovarian cancer, prostate cancer and uterine leiomyosarcoma.

As used herein the term 'leukemia' refers to neoplastic diseases of the blood and blood forming organs. Such diseases can cause bone marrow and immune system dysfunction, which renders the host highly susceptible to infection and bleeding. In particular the term leukemia refers to acute myeloid leukaemia (AML) and acute lymphoblastic leukemia (ALL).

As used herein the term 'transplantation rejection' refers to the acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases.

As used herein the term 'diseases involving impairment of cartilage turnover' includes conditions such as osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis.

As used herein the term 'congenital cartilage malformation(s)' includes conditions such as hereditary chondrolysis, chondrodysplasias and pseudochondrodysplasias, in particular, but without limitation, microtia, anotia, metaphyseal chondrodysplasia, and related disorders.

As used herein the term 'disease(s) associated with hypersecretion of IL6' includes conditions such as Castleman's disease, multiple myeloma, psoriasis, Kaposi's sarcoma and/or mesangial proliferative glomerulonephritis.

As used herein the term 'disease(s) associated with hypersecretion of interferons' includes conditions such as systemic and cutaneous lupus erythematosis, lupus nephritis, dermatomyositis, Sjogren's syndrome, psoriasis, rheumatoid arthritis.

'Compound of the invention', and equivalent expressions, are meant to embrace the compound according to Formula I or Formula II (as context dictates) as hereinbefore described, which expression includes the pharmaceutically acceptable salts, and the solvates, e.g., hydrates, and the solvates of the pharmaceutically acceptable salts where the context so permits. Similarly, reference to intermediates, whether or not they themselves are claimed, is meant to embrace their salts, and solvates, where the context so permits.

Other derivatives of the compound of the invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985).

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radio-isotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compound provided herein, radioactive or not, are intended to be encompassed within the scope of the invention.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

THE INVENTION

The present invention is based on the discovery that the compound of the invention according to Formula I may be useful as a medicament. In a particular aspect, the compound of the invention according to Formula I is an inhibitor of JAK, and more particularly JAK1.

The present invention also provides methods for the production of the compound of the invention according to Formula I, pharmaceutical compositions comprising the compound of the invention according to Formula I and methods for the prophylaxis and/or treatment of inflammatory conditions, autoimmune diseases, proliferative diseases, allergy, transplant rejection, diseases involving impairment of cartilage turnover, congenital cartilage malformations, and/or diseases associated with hypersecretion of IL6 or interferons, in particular rheumatoid arthritis, by administering the compound of the invention according to Formula I.

Accordingly, in a first embodiment of the invention, a compound of the invention according to Formula I is provided for use in medicine having a Formula I:

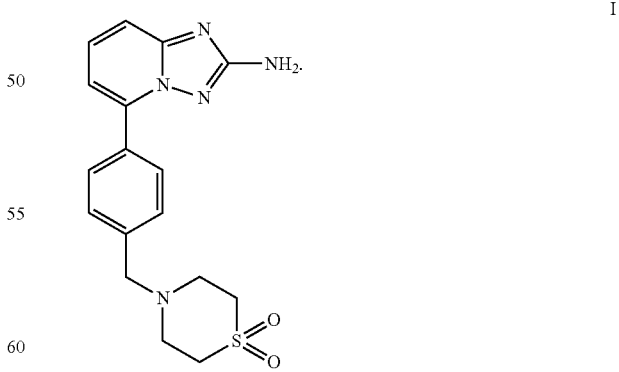

In another embodiment, the compound of the invention may be prepared in a therapeutic combination, with a further therapeutically active ingredient. The further therapeutically active ingredient may be a compound for the treatment of the same conditions and diseases outlined herein with respect to the compound of formula I. In a particular embodiment, the further therapeutically active ingredient may be a compound for the treatment of arthritis. In a most particular aspect, the further therapeutically active ingredient is a compound for the treatment of rheumatoid arthritis.

In another embodiment of the invention, a compound of the invention, which is a JAK inhibitor, is provided for use in medicine having a Formula I:

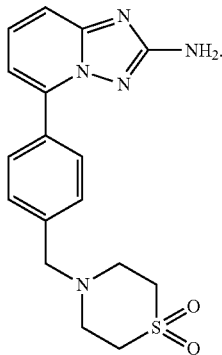

I

The compound of the invention according to Formula I, surprisingly, exhibits in vivo in humans a very different profile from other animal species, which contrasts with in vitro predictions. Indeed, in vivo, it has been demonstrated that in humans, the apparent terminal half life of the compound of the invention according to Formula I is significantly longer than in the other animal species by at least 3 fold. This causes accumulation in humans resulting in a maintained therapeutic effect over an extended period of time, thereby allowing once daily to once weekly dosing. Thus the compound of the invention according to Formula I may provide advantages including a low frequency dosage regimen and/or increased patient compliance. In particular, the impact of non adherence, if the patient misses a dose might be reduced.

In one embodiment the compound of the invention according to Formula I is not an isotopic variant.

In one aspect the compound of the invention according to Formula I is present as the free base.

In one aspect the compound of the invention according to Formula I is a pharmaceutically acceptable salt.

In one aspect the compound of the invention according to Formula I is a solvate of the compound of the invention according to Formula I.

In one aspect the compound of the invention according to Formula I is a solvate of a pharmaceutically acceptable salt of a compound of the invention according to Formula I.

The compound of the invention according to Formula I is an inhibitor of JAK. In particular the compound of the invention according to Formula I is a potent inhibitor of JAK1, however it may inhibit JAK2, JAK3 and TYK2 with a lower potency.

In a further embodiment, the present invention provides a pharmaceutical composition comprising the compound of the invention according to Formula I, and a pharmaceutical carrier, excipient or diluent.

In yet a further embodiment, the pharmaceutical composition further comprises an additional therapeutic agent. In a particular aspect, the other compound is a compound for the treatment of arthritis. In a more particular aspect, the other compound is a compound for the treatment of rheumatoid arthritis. In a most particular embodiment, the further therapeutic agent is a compound of the invention according to Formula II:

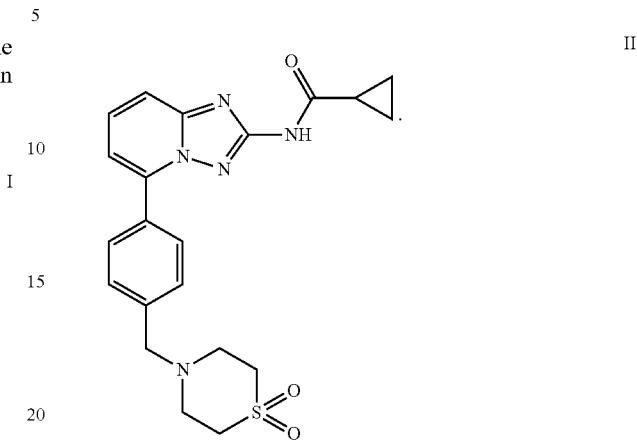

II

Pharmaceutical Compositions

When employed as a pharmaceutical, the compound of the invention according to Formula I is typically administered in the form of a pharmaceutical composition. Such compositions can be prepared in a manner well known in the pharmaceutical art and comprise at least one active compound of the invention according to Formula I. Generally, the compound of the invention according to Formula I is administered in a pharmaceutically effective amount. The amount of the compound of the invention according to Formula I actually administered will typically be determined by a physician, in the light of the relevant circumstances, including the condition to be treated, the chosen route of administration, the actual compound of the invention according to Formula I administered, the age, weight, and response of the individual patient, the severity of the patient's symptoms, and the like.

The pharmaceutical compositions of this invention can be administered by a variety of routes including oral, rectal, transdermal, subcutaneous, intra-articular, intravenous, intramuscular, and intranasal. Depending on the intended route of delivery, the compound of the invention according to Formula I of this invention is preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term 'unit dosage forms' refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, the compound of the invention according to Formula I is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compound of the inventions of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint or orange flavoring.

Injectable compositions are typically based upon injectable sterile saline or phosphate-buffered saline or other injectable carriers known in the art. As before, the active compound of the invention according to Formula I in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compound of the invention according to Formula I can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17$^{th}$ edition, 1985, Mack Publishing Company, Easton, Pa., which is incorporated herein by reference.

The compound of the invention according to Formula I can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1

Tablets

The compound of the invention according to Formula I may be admixed as a dry powder with a dry gelatin binder in an approximate 1:2 weight ratio. A minor amount of magnesium stearate may be added as a lubricant. The mixture may be formed into 240-270 mg tablets (80-90 mg of active compound of the invention according to Formula I per tablet) in a tablet press.

Formulation 2

Capsules

The compound of the invention according to Formula I may be admixed as a dry powder with a starch diluent in an approximate 1:1 weight ratio. The mixture may be filled into 250 mg capsules (125 mg of active compound of the invention according to Formula I per capsule).

Formulation 3

Liquid

The compound of the invention according to Formula I (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color may be diluted with water and added with stirring. Sufficient water may then be added with stirring. Further sufficient water may be then added to produce a total volume of 5 mL.

Formulation 4

Tablets

The compound of the invention according to Formula I may be admixed as a dry powder with a dry gelatin binder in an approximate 1:2 weight ratio. A minor amount of magnesium stearate may be added as a lubricant. The mixture may be formed into 450-900 mg tablets (150-300 mg of active compound of the invention according to Formula I) in a tablet press.

Formulation 5

Injection

The compound of the invention according to Formula I may be dissolved or suspended in a buffered sterile saline injectable aqueous medium to a concentration of approximately 5 mg/mL.

Formulation 6

Topical

Stearyl alcohol (250 g) and a white petrolatum (250 g) may be melted at about 75° C. and then a mixture of the compound of the invention according to Formula I (50 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

In one embodiment, the present invention provides a pharmaceutical composition comprising the compound of the invention according to Formula I, for use in medicine. In a particular embodiment, the present invention provides a pharmaceutical composition comprising the compound of the invention according to Formula I, for use in the prophylaxis and/or treatment of inflammatory conditions, autoimmune diseases, proliferative diseases, allergy, transplant rejection, diseases involving impairment of cartilage turnover, congenital cartilage malformations, and/or diseases associated with hypersecretion of IL6 or interferons, in particular rheumatoid arthritis.

In another embodiment, the present invention provides a pharmaceutical composition comprising the compound of the invention according to Formula I, for use in the manufacture of a medicament for use in the prophylaxis and/or treatment of inflammatory conditions, autoimmune diseases, proliferative diseases, allergy, transplant rejection, diseases involving impairment of cartilage turnover, congenital cartilage malformations, and/or diseases associated with hypersecretion of IL6 or interferons, in particular rheumatoid arthritis.

In one embodiment, the present invention provides a pharmaceutical composition comprising the compound of the invention according to Formula I, and another therapeutic agent. In a particular embodiment, the other therapeutic agent is an arthritis treatment agent. In a more particular embodiment, the other therapeutic agent is a rheumatoid arthritis treatment agent. In a most particular embodiment, the other therapeutic agent is the compound according to Formula II.

In additional method of treatment aspects, this invention provides methods of prophylaxis and/or treatment of a mammal susceptible to or afflicted with an inflammatory condition, which methods comprise the administration of a therapeutically effective amount of the compound of the invention according to Formula I or one or more of the pharmaceutical compositions herein described for the treatment or prophylaxis of said condition. In a specific embodiment, the inflammatory condition is selected from rheumatoid arthritis, osteoarthritis, allergic airway disease (e.g. asthma) and inflammatory bowel diseases (e.g. Crohn's disease or ulcerative colitis).

In another aspect the present invention provides the compound of the invention according to Formula I or a pharmaceutical composition comprising the compound of the invention according to Formula I for use in the treatment or prophylaxis of an inflammatory condition. In a specific embodiment, the inflammatory condition is selected from rheumatoid arthritis, osteoarthritis, allergic airway disease (e.g. asthma) and inflammatory bowel diseases.

In another aspect the present invention provides the compound of the invention according to Formula I or a pharmaceutical composition comprising the compound of the invention according to Formula I for use in the manufacture of a medicament for the treatment or prophylaxis of an inflammatory condition. In a specific embodiment, the inflammatory condition is selected from rheumatoid arthritis, osteoarthritis, allergic airway disease (e.g. asthma) and inflammatory bowel diseases (e.g. Crohn's disease or ulcerative colitis).

In a method of treatment aspects, this invention provides methods of treatment or prophylaxis of a mammal susceptible to or afflicted with an allergic reaction, which methods comprise the administration of a therapeutically effective amount of one or more of the pharmaceutical compositions or compound of the invention according to Formula I herein described for the treatment or prophylaxis of said condition. In a specific embodiment, the invention provides methods of treatment or prophylaxis of allergic airway disease, sinusitis, eczema and/or hives, food allergies or allergies to insect venom.

In another aspect the present invention provides the compound of the invention according to Formula I or a pharmaceutical composition comprising the compound of the invention according to Formula I, for use in the treatment or prophylaxis of an allergic reaction. In a specific embodiment, the invention provides methods of treatment or prophylaxis of allergic airway disease, sinusitis, eczema and/or hives, food allergies or allergies to insect venom.

In another aspect the present invention provides the compound of the invention according to Formula I or a pharmaceutical composition comprising the compound of the invention according to Formula I, for use in the manufacture of a medicament for the treatment or prophylaxis of an allergic reaction. In a specific embodiment, the invention provides methods of treatment or prophylaxis of allergic airway disease, sinusitis, eczema and/or hives, food allergies or allergies to insect venom.

In additional method of treatment aspects, this invention provides methods of treatment or prophylaxis of a mammal susceptible to or afflicted with an autoimmune disease, which methods comprise the administration of a therapeutically effective amount of one or more of the pharmaceutical compositions or compound of the invention according to Formula I herein described for the treatment or prophylaxis of said condition. In a specific embodiment, the autoimmune disease is selected from rheumatoid arthritis, COPD, asthma, systemic lupus erythematosus, type I diabetes mellitus, psoriatic arthritis, ankylosing spondylitis, juvenile ideopathic arthritis, and inflammatory bowel disease (e.g. Crohn's disease or ulcerative colitis). In a more specific embodiment, the autoimmune disease is systemic lupus erythematosus. In yet another more specific embodiment, autoimmune disease is rheumatoid arthritis or psoriatic arthritis. In yet a further specific embodiment, autoimmune disease is inflammatory bowel disease (e.g. Crohn's disease or ulcerative colitis).

In another aspect the present invention provides the compound of the invention according to Formula I or a pharmaceutical composition comprising the compound of the invention according to Formula I, for use in the treatment or prophylaxis of an autoimmune disease. In a specific embodiment, the autoimmune disease is selected from rheumatoid arthritis, COPD, asthma, systemic lupus erythematosus, type I diabetes mellitus, psoriatic arthritis, ankylosing spondylitis, juvenile ideopathic arthritis, and inflammatory bowel disease (e.g. Crohn's disease or ulcerative colitis). In a more specific embodiment, the autoimmune disease is systemic lupus erythematosus. In yet another more specific embodiment, autoimmune disease is rheumatoid arthritis or psoriatic arthritis. In yet a further specific embodiment, autoimmune disease is inflammatory bowel disease (e.g. Crohn's disease or ulcerative colitis).

In another aspect the present invention provides the compound of the invention according to Formula I or a pharmaceutical composition comprising the compound of the invention according to Formula I, for use in the manufacture of a medicament for the treatment or prophylaxis of an autoimmune disease. In a specific embodiment, the autoimmune disease is selected from rheumatoid arthritis, COPD, asthma, systemic lupus erythematosus, type I diabetes mellitus, psoriatic arthritis, ankylosing spondylitis, juvenile ideopathic arthritis, and inflammatory bowel disease (e.g. Crohn's disease or ulcerative colitis). In a more specific embodiment, the autoimmune disease is systemic lupus erythematosus. In yet another more specific embodiment, autoimmune disease is rheumatoid arthritis or psoriatic arthritis. In yet a further specific embodiment, autoimmune disease is inflammatory bowel disease (e.g. Crohn's disease or ulcerative colitis).

In further method of treatment aspects, this invention provides methods of treatment or prophylaxis of a mammal susceptible to or afflicted with a proliferative disease, which methods comprise the administration of a therapeutically effective amount of one or more of the pharmaceutical compositions or compound of the invention according to Formula I herein described for the treatment or prophylaxis of said condition. In a specific embodiment, the proliferative disease is cancer (e.g. solid tumors such as uterine leiomyosarcoma or prostate cancer), cutaneous T-cell lymphoma, breast cancer, leukemia (e.g. AML, ALL or CLL), multiple myeloma and/or psoriasis. In a more specific embodiment, the proliferative disease is psoriasis.

In another aspect the present invention provides the compound of the invention according to Formula I or a pharmaceutical composition comprising the compound of the invention according to Formula I, for use in the treatment or prophylaxis of a proliferative disease. In a specific embodiment, the proliferative disease is cancer (e.g. solid tumors such as uterine leiomyosarcoma or prostate cancer), cutaneous T-cell lymphoma, breast cancer, leukemia (e.g. AML, ALL or CLL), multiple myeloma and/or psoriasis. In a more specific embodiment, the proliferative disease is psoriasis.

In another aspect the present invention provides the compound of the invention according to Formula I or a pharmaceutical composition comprising the compound of the invention according to Formula I, for use in the manufacture of a medicament for the treatment or prophylaxis of a proliferative disease. In a specific embodiment, the proliferative disease is cancer (e.g. solid tumors such as uterine leiomyosarcoma or prostate cancer), cutaneous T-cell lymphoma, breast cancer, leukemia (e.g. AML, ALL or CLL), multiple myeloma and/or psoriasis. In a more specific embodiment, the proliferative disease is psoriasis.

In further method of treatment aspects, this invention provides methods of treatment or prophylaxis of a mammal susceptible to or afflicted with transplant rejection, which methods comprise the administration of a therapeutically effective amount of one or more of the pharmaceutical compositions, therapeutic combinations or compound of the invention according to Formula I herein described for the treatment or prophylaxis of said condition. In a specific embodiment, the invention provides methods of treatment or prophylaxis of organ transplant rejection.

In another aspect the present invention provides the compound of the invention according to Formula I or a pharmaceutical composition comprising the compound of the invention according to Formula I for use in the treatment or prophylaxis of transplant rejection. In a specific embodiment, the invention provides methods of treatment or prophylaxis of organ transplant rejection.

In another aspect the present invention provides the compound of the invention according to Formula I or a pharmaceutical composition comprising the compound of the invention according to Formula I for use in the manufacture of a medicament for the treatment or prophylaxis of transplant rejection. In a specific embodiment, the invention provides methods of treatment or prophylaxis of organ transplant rejection.

In a method of treatment aspect, this invention provides a method of treatment or prophylaxis in a mammal susceptible to or afflicted with diseases involving impairment of cartilage turnover, which methods comprise the administration of a therapeutically effective amount of one or more of the pharmaceutical compositions or compound of the invention according to Formula I herein described for the treatment or prophylaxis of said condition.

In another aspect the present invention provides the compound of the invention according to Formula I or a pharmaceutical composition comprising the compound of the invention according to Formula I for use in the treatment or prophylaxis of diseases involving impairment of cartilage turnover.

The present invention also provides a method of treatment or prophylaxis of congenital cartilage malformations, which methods comprise the administration of a therapeutically effective amount of one or more of the pharmaceutical compositions or compound of the invention according to Formula I herein described for the treatment or prophylaxis of said condition.

In another aspect the present invention provides the compound of the invention according to Formula I or a pharmaceutical composition comprising the compound of the invention according to Formula I for use in the treatment or prophylaxis of congenital cartilage malformations.

In further method of treatment aspects, this invention provides methods of treatment or prophylaxis of a mammal susceptible to or afflicted with diseases associated with hypersecretion of IL6, which methods comprise the administration of a therapeutically effective amount of one or more of the pharmaceutical compositions or compound of the invention according to Formula I herein described for the treatment or prophylaxis of said condition. In a specific embodiment, the disease associated with hypersecretion of IL6, is selected from Castleman's disease and mesangial proliferative glomerulonephritis.

In another aspect the present invention provides the compound of the invention according to Formula I or a pharmaceutical composition comprising the compound of the invention according to Formula I for use in the treatment or prophylaxis of diseases associated with hypersecretion of IL6. In a specific embodiment, the disease associated with hypersecretion of IL6, is selected from Castleman's disease and mesangial proliferative glomerulonephritis.

In further method of treatment aspects, this invention provides methods of treatment or prophylaxis of a mammal susceptible to or afflicted with diseases associated with hypersecretion of interferons, which methods comprise the administration of a therapeutically effective amount of one or more of the pharmaceutical compositions or compound of the invention according to Formula I herein described for the treatment or prophylaxis of said condition. In a specific embodiment, the disease associated with hypersecretion of interferon, is selected from systemic and cutaneous lupus erythematosus, lupus nephritis, dermatomyositis, Sjogren's syndrome, psoriasis, and rheumatoid arthritis.

In another aspect the present invention provides the compound of the invention according to Formula I or a pharmaceutical composition comprising the compound of the invention according to Formula I for use in the treatment or prophylaxis of diseases associated with hypersecretion of interferons. In a specific embodiment, the disease associated with hypersecretion of interferon, is selected from systemic and cutaneous lupus erythematosus, lupus nephritis, dermatomyositis, Sjogren's syndrome, psoriasis, and rheumatoid arthritis.

A particular regimen of the present method comprises the administration to a subject suffering from a disease involving inflammation, in particular rheumatoid arthritis, osteoarthritis, allergic airway disease (e.g. asthma) and/or inflammatory bowel diseases, of a therapeutically effective amount of the compound of the invention according to Formula I for a period of time sufficient to reduce the level of inflammation in the subject, and preferably terminate the processes responsible for said inflammation. A special embodiment of the method comprises administering of a therapeutically effective amount of the compound of the invention according to Formula I to a subject patient suffering from or susceptible to the development of rheumatoid arthritis, for a period of time sufficient to reduce or prevent, respectively, inflammation in the joints of said patient, and preferably terminate, the processes responsible for said inflammation.

A further particular regimen of the present method comprises the administration to a subject suffering from a disease or condition characterized by cartilage or joint degradation (e.g. rheumatoid arthritis and/or osteoarthritis) of a therapeutically effective amount of the compound of the invention according to Formula I for a period of time sufficient to reduce and preferably terminate the self-perpetuating processes responsible for said degradation. A particular embodiment of the method comprises administering of a therapeutically effective amount of the compound of the invention according to Formula I to a subject patient suffering from or susceptible to the development of osteoarthritis, for a period of time sufficient to reduce or prevent, respectively, cartilage degradation in the joints of said patient, and preferably terminate, the self-perpetuating processes responsible for said degradation. In a particular embodiment said compound of the invention according to Formula I may exhibit cartilage anabolic and/or anti-catabolic properties.

In one aspect, the present invention provides a compound of the invention according to Formula I for use in the prophylaxis and/or treatment of inflammatory conditions, autoimmune diseases, proliferative diseases, allergy, transplant rejection, diseases involving impairment of cartilage turnover, congenital cartilage malformations, and/or diseases associated with hypersecretion of IL6 or interferons, in particular rheumatoid arthritis, wherein the compound is administered in one to four (1-4) regular doses daily and especially one to three (1-3) regular doses daily, typically one to two (1-2) regular doses daily, and most typically one (1) regular dose daily.

In another aspect, the present invention provides a compound of the invention according to Formula I for use in the prophylaxis and/or treatment of inflammatory conditions, autoimmune diseases, proliferative diseases, allergy, transplant rejection, diseases involving impairment of cartilage turnover, congenital cartilage malformations, and/or diseases associated with hypersecretion of IL6 or interferons, in particular rheumatoid arthritis, wherein the compound is administered in one to thirteen (1-13) regular doses in a two-week period. In a specific embodiment, the compound according to Formula I is administered in one to twelve (1-12), one to ten (1-10) or two-seven (2-7) regular doses in a two week period. In a specific embodiment the compound of the invention according to Formula I is administered on a once-weekly basis.

In a further aspect, the present invention provides a compound of the invention according to Formula II for use in the prophylaxis and/or treatment of inflammatory conditions, autoimmune diseases, proliferative diseases, allergy, transplant rejection, diseases involving impairment of cartilage turnover, congenital cartilage malformations, and/or diseases associated with hypersecretion of IL6 or interferons, in particular rheumatoid arthritis, wherein the compound is administered in one to thirteen (1-13) regular doses in a two-week period. In a specific embodiment, the compound according to Formula II is administered in one to twelve (1-12), one to ten (1-10) or two-seven (2-7) regular doses in a two week period. In a specific embodiment the compound of the invention according to Formula II is administered on a once-weekly basis.

In yet a further aspect, the present invention provides a combination of a compound of the invention according to Formula I and a compound of the invention according to Formula II for use in the prophylaxis and/or treatment of inflammatory conditions, autoimmune diseases, proliferative diseases, allergy, transplant rejection, diseases involving impairment of cartilage turnover, congenital cartilage malformations, and/or diseases associated with hypersecretion of IL6 or interferons, in particular rheumatoid arthritis, wherein the compound is administered in one to four (1-4) regular doses daily and especially one to three (1-3) regular doses daily, typically one to two (1-2) regular doses daily, and most typically one (1) regular dose daily.

In yet a another further aspect, the present invention provides a combination of a compound of the invention according to Formula I and a compound of the invention according to Formula II for use in the prophylaxis and/or treatment of inflammatory conditions, autoimmune diseases, proliferative diseases, allergy, transplant rejection, diseases involving impairment of cartilage turnover, congenital cartilage malformations, and/or diseases associated with hypersecretion of IL6 or interferons, in particular rheumatoid arthritis, wherein the compound is administered in one to thirteen (1-13) regular doses in a two-week period. In a specific embodiment, a combination of a compound of the invention according to Formula I and a compound of the invention according to Formula II is administered in one to twelve (1-12), one to ten (1-10) or two-seven (2-7) regular doses in a two week period. In a specific embodiment a combination of a compound of the invention according to Formula I and a compound of the invention according to Formula II is administered on a once-weekly basis.

Injection dose levels range from about 0.1 mg/kg/h to at least 10 mg/kg/h, all for from about 1 to about 120 h and especially 24 to 96 h. A preloading bolus of from about 0.1 mg/kg to about 10 mg/kg or more may also be administered to achieve adequate steady state levels. The maximum total dose is not expected to exceed about 1 g/day for a 40 to 80 kg human patient.

For the prophylaxis and/or treatment of long-term conditions, such as degenerative conditions, the regimen for treatment usually stretches over many months or years so oral dosing is preferred for patient convenience and tolerance. With oral dosing, one to four (1-4) regular doses daily, especially one to three (1-3) regular doses daily, typically one to two (1-2) regular doses daily, and most typically one (1) regular dose daily are representative regimens. Alternatively for long lasting effect drugs, with oral dosing, once every other week, once weekly, and once a day are representative regimens. In particular, dosage regimen can be every 1-14 days, more particularly 1-10 days, even more particularly 1-7 days, and most particularly 1-3 days.

Using these dosing patterns, each dose provides from about 1 to about 1000 mg of the compound of the invention according to Formula I, with particular doses each providing from about 10 to about 500 mg and especially about 30 to about 250 mg.

Using these dosing patterns, each dose provides from about 1 to about 1000 mg of the compound of the invention according to Formula II, with particular doses each providing from about 10 to about 500 mg and especially about 30 to about 250 mg.

Transdermal doses are generally selected to provide similar or lower blood levels than are achieved using injection doses.

When used to prevent the onset of a condition, the compound of the invention according to Formula I will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compound of the invention according to Formula I can be administered as the sole active agent or it can be administered in combination with other therapeutic agents, including other compound of the inventions that demonstrate the same or a similar therapeutic activity and that are determined to safe and efficacious for such combined administration. In a specific embodiment, co-administration of two (or more) agents allows for significantly lower doses of each to be used, thereby reducing the side effects seen.

In one embodiment, the compound of the invention according to Formula I or a pharmaceutical composition comprising the compound of the invention according to Formula I is administered as a medicament. In a specific embodiment, said pharmaceutical composition additionally comprises a further active ingredient.

In one embodiment, the compound of the invention according to Formula I is co-administered with another therapeutic agent for the treatment and/or prophylaxis of a disease involving inflammation; particular agents include, but are not limited to, immunoregulatory agents e.g. azathioprine, corticosteroids (e.g. prednisolone or dexamethasone), cyclophosphamide, cyclosporin A, tacrolimus, Mycophenolate Mofetil, muromonab-CD3 (OKT3, e.g. Orthocolone®), ATG, aspirin, acetaminophen, ibuprofen, naproxen, and piroxicam.

In one embodiment, the compound of the invention according to Formula I is co-administered with another therapeutic agent for the treatment and/or prophylaxis of arthritis (e.g. rheumatoid arthritis); particular agents include but are not limited to analgesics, non-steroidal anti-inflammatory drugs (NSAIDS), steroids, synthetic DMARDS (for example but without limitation methotrexate, leflunomide, sulfasalazine, auranofin, sodium aurothiomalate, penicillamine, chloroquine, hydroxychloroquine, azathioprine, tofacitinib, baricitinib, fostamatinib, and cyclosporin), and biological DMARDS (for example but without limitation Infliximab, Etanercept, Adalimumab, Rituximab, and Abatacept).

In one embodiment, the compound of the invention according to Formula I is co-administered with another therapeutic agent for the treatment and/or prophylaxis of proliferative disorders; particular agents include but are not limited to: methotrexate, leukovorin, adriamycin, prednisone, bleomycin, cyclophosphamide, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibody (e.g. Herceptin™), capecitabine, raloxifene hydrochloride, EGFR inhibitors (e.g. Iressa®, Tarceva™, Erbitux™), VEGF inhibitors (e.g. Avastin™), proteasome inhibitors (e.g. Velcade™), Glivec® and hsp90 inhibitors (e.g. 17-AAG). Additionally, the compound of the invention according to Formula I may be administered in combination with other therapies including, but not limited to, radiotherapy or surgery. In a specific embodiment the proliferative disorder is selected from cancer, myeloproliferative disease or leukaemia.

In one embodiment, the compound of the invention according to Formula I is co-administered with another therapeutic agent for the treatment and/or prophylaxis of autoimmune diseases, particular agents include but are not limited to: glucocorticoids, cytostatic agents (e.g. purine analogs), alkylating agents, (e.g nitrogen mustards (cyclophosphamide), nitrosoureas, platinum compound of the inventions, and others), antimetabolites (e.g. methotrexate, azathioprine and mercaptopurine), cytotoxic antibiotics (e.g. dactinomycin anthracyclines, mitomycin C, bleomycin, and mithramycin), antibodies (e.g. anti-CD20, anti-CD25 or anti-CD3 (OTK3) monoclonal antibodies, Atgam® and Thymoglobuline®), cyclosporin, tacrolimus, rapamycin (sirolimus), interferons (e.g. IFN-β), TNF binding proteins (e.g. infliximab, etanercept, or adalimumab), mycophenolate, Fingolimod and Myriocin.

In one embodiment, the compound of the invention according to Formula I is co-administered with another therapeutic agent for the treatment and/or prophylaxis of transplant rejection, particular agents include but are not limited to: calcineurin inhibitors (e.g. cyclosporin or tacrolimus (FK506)), mTOR inhibitors (e.g. sirolimus, everolimus), anti-proliferatives (e.g. azathioprine, mycophenolic acid), corticosteroids (e.g. prednisolone, hydrocortisone), Antibodies (e.g. monoclonal anti-IL-2Rα receptor antibodies, basiliximab, daclizumab), polyclonal anti-T-cell antibodies (e.g. anti-thymocyte globulin (ATG), anti-lymphocyte globulin (ALG)).

In one embodiment, the compound of the invention according to Formula I is co-administered with another therapeutic agent for the treatment and/or prophylaxis of asthma and/or rhinitis and/or COPD, particular agents include but are not limited to: beta2-adrenoceptor agonists (e.g. salbutamol, levalbuterol, terbutaline and bitolterol), epinephrine (inhaled or tablets), anticholinergics (e.g. ipratropium bromide), glucocorticoids (oral or inhaled) Long-acting β2-agonists (e.g. salmeterol, formoterol, bambuterol, and sustained-release oral albuterol), combinations of inhaled steroids and long-acting bronchodilators (e.g. fluticasone/salmeterol, budesonide/formoterol), leukotriene antagonists and synthesis inhibitors (e.g. montelukast, zafirlukast and zileuton), inhibitors of mediator release (e.g. cromoglycate and ketotifen), biological regulators of IgE response (e.g. omalizumab), antihistamines (e.g. ceterizine, cinnarizine, fexofenadine) and vasoconstrictors (e.g. oxymethazoline, xylomethazoline, nafazoline and tramazoline).

Additionally, the compound of the invention according to Formula I may be administered in combination with emergency therapies for asthma and/or COPD, such therapies include oxygen or heliox administration, nebulized salbutamol or terbutaline (optionally combined with an anticholinergic (e.g. ipratropium), systemic steroids (oral or intravenous, e.g. prednisone, prednisolone, methylprednisolone, dexamethasone, or hydrocortisone), intravenous salbutamol, non-specific beta-agonists, injected or inhaled (e.g. epinephrine, isoetharine, isoproterenol, metaproterenol), anticholinergics (IV or nebulized, e.g. glycopyrrolate, atropine, ipratropium), methylxanthines (theophylline, aminophylline, bamiphylline), inhalation anesthetics that have a bronchodilatory effect (e.g. isoflurane, halothane, enflurane), ketamine and intravenous magnesium sulfate.

In one embodiment, the compound of the invention according to Formula I is co-administered with another therapeutic agent for the treatment and/or prophylaxis of inflammatory bowel disease (IBD), particular agents include but are not limited to: glucocorticoids (e.g. prednisone, budesonide) synthetic disease modifying, immunomodulatory agents (e.g. methotrexate, leflunomide, sulfasalazine, mesalazine, azathioprine, 6-mercaptopurine and cyclosporin) and biological disease modifying, immunomodulatory agents (infliximab, adalimumab, rituximab, and abatacept).

In one embodiment, the compound of the invention according to Formula I is co-administered with another therapeutic agent for the treatment and/or prophylaxis of SLE, particular agents include but are not limited to: Disease-modifying antirheumatic drugs (DMARDs) such as antimalarials (e.g. plaquenil, hydroxychloroquine), immunosuppressants (e.g. methotrexate and azathioprine), cyclophosphamide and mycophenolic acid; immunosuppressive drugs and analgesics, such as nonsteroidal anti-inflammatory drugs, opiates (e.g. dextropropoxyphene and co-codamol), opioids (e.g. hydrocodone, oxycodone, MS Contin, or methadone) and the fentanyl duragesic transdermal patch.

In one embodiment, the compound of the invention according to Formula I is co-administered with another therapeutic agent for the treatment and/or prophylaxis of psoriasis, particular agents include but are not limited to: topical treatments such as bath solutions, moisturizers, medicated creams and ointments containing coal tar, dithranol (anthralin), corticosteroids like desoximetasone (Topicort™), fluocinonide, vitamin D3 analogues (for example, calcipotriol), Argan oil and retinoids (etretinate, acitretin, tazarotene), systemic treatments such as methotrexate, cyclosporine, retinoids, tioguanine, hydroxyurea, sulfasalazine, mycophenolate mofetil, azathioprine, tacrolimus, fumaric acid esters or biologics such as Amevive™, Enbrel™, Humira™, Remicade™ Raptiva™ and ustekinumab (a IL-12 and IL-23 blocker). Additionally, the compound of the invention according to Formula I may be administered in combination with other therapies including, but not limited to phototherapy, or photochemotherapy (e.g. psoralen and ultraviolet A phototherapy (PUVA)).

In one embodiment, the compound of the invention according to Formula I is co-administered with another therapeutic agent for the treatment and/or prophylaxis of allergic reaction, particular agents include but are not limited to: antihistamines (e.g. cetirizine, diphenhydramine, fexofenadine, levocetirizine), glucocorticoids (e.g. prednisone, betamethasone, beclomethasone, dexamethasone), epinephrine, theophylline or anti-leukotrienes (e.g. montelukast or zafirlukast), anticholinergics and decongestants.

By co-administration is included any means of delivering two or more therapeutic agents to the patient as part of the same treatment regime, as will be apparent to the skilled person. Whilst the two or more agents may be administered simultaneously in a single formulation, i.e. as a single pharmaceutical composition, this is not essential. The agents may be administered in different formulations and at different times.

In one embodiment, the present invention provides a pharmaceutical composition comprising the compound of the invention according to Formula I, and the compound according to Formula II, wherein the ratio of the compound of the invention according to Formula I/Formula II is from 1/5 to 1/20. In a particular embodiment, the ratio is from 1/5 to 1/10.

General Synthetic Procedures

General

The compound of the invention according to Formula I can be prepared from readily available starting materials using the following general methods and procedures. It will be appreciated that where typical or preferred process conditions (i.e. reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, Protecting Groups in Organic Synthesis, Second Edition, Wiley, New York, 1991, and references cited therein.

The following methods are presented with details as to the preparation of the compound of the invention according to Formula I as defined hereinabove and the comparative examples. The compound of the invention according to Formula I may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica gel 60 (35-70 µm). Thin layer chromatography was carried out using pre-coated silica gel F-254 plates (thickness 0.25 mm) $^1$H NMR spectra were recorded on a Bruker DPX 400 NMR spectrometer (400 MHz). Chemical shifts (δ) for $^1$H NMR spectra are reported in parts per million (ppm) relative to tetramethylsilane (δ 0.00) or the appropriate residual solvent peak, i.e. CHCl$_3$ (δ 7.27), as internal reference. Multiplicities are given as singlet (s), doublet (d), triplet (t), quartet (q), multiplet (m) and broad (br). Coupling constants (J) are given in Hz. Electrospray MS spectra were obtained on a Micromass platform LC/MS spectrometer. Columns Used for LCMS analysis: Hichrom, Kromasil Eternity, 2.5 µm C$_{18}$, 150×4.6 mm, Waters Xbridge 5 µm C$_{18}$ (2), 250×4.6 mm (ref 86003117), Waters Xterra MS 5 µm C$_{18}$, 100×4.6 mm (Plus guard cartridge) (ref 186000486), Gemini-NX 3 µm C$_{18}$ 100× 3.0 mm (ref 00D-4453-Y0), Phenomenex Luna 5 µm C$_{18}$ (2), 100×4.6 mm. (Plus guard cartridge) (ref 00D-4252-E0), Kinetix fused core 2.7 µm C$_{18}$ 100×4.6 mm (ref 00D-4462-E0), Supelco, Ascentis® Express C$_{18}$ (ref 53829-U), or Hichrom Halo C$_{18}$, 2.7 µm C$_{18}$, 150×4.6 mm (ref 92814-702). LC-MS were recorded on a Waters Micromass ZQ coupled to a HPLC Waters 2795, equipped with a UV detector Waters 2996. LC were also run on a HPLC Agilent 1100 coupled to a UV detector Agilent G1315A. Preparative HPLC: Waters XBridge Prep C$_{18}$ 5 µm ODB 19 mm ID×100 mm L (Part No. 186002978). All the methods are using MeCN/H$_2$O gradients. H$_2$O contains either 0.1% TFA or 0.1% NH$_3$.

List of abbreviations used in the experimental section:

| | | | |
|---|---|---|---|
| AUC | Area Under the Curve | DiPEA | N,N-diisopropylethylamine |
| APC | Adenomatous Polyposis Coli | MeCN | Acetonitrile |
| DCM | Dichloromethane | DMF | N,N-dimethylformamide |
| Cat. | Catalytic amount | PdCl$_2$dppf | [1,1'-Bis(diphenylphosphino)ferrocene]dichloropalladium(II) |
| TFA | Trifluoroacetic acid | | |
| THF | Tetrahydrofuran | MMP | Matrix Metallo Proteinase |
| NMR | Nuclear Magnetic Resonnance | RNA | Ribonucleic acid |
| DMSO | Dimethylsulfoxide | APMA | 4-aminophenylmercuric acetate |
| LC-MS | Liquid Chromatography-Mass Spectrometry | FBS | Fetal bovine serum |
| | | cDNA | copy deoxyribonucleic acid |
| ppm | part-per-million | h | hour |
| EtOAc | ethyl acetate | FITC | Fluorescein Isothiocyanate |
| Rt | retention time | mmol | millimoles |
| s | singlet | QD | Quaque Die (once daily dosing) |
| br s | broad singlet | BID | Bis in Die (twice daily) |
| m | multiplet | Rel. | Relative |
| min | minute | HPLC | High pressure liquid chromatography |
| mL | milliliter | | |
| µL | microliter | | |
| g | gram | | |
| mg | milligram | | |

Synthetic Preparation of the Compound of the Invention

Example 1

Synthesis of the Compounds 1.1. Route 1

1.1.1. Synthesis of 5-Bromo-[1,2,4]triazolo[1,5-a]pyridin-2-ylamine (Intermediate 3)

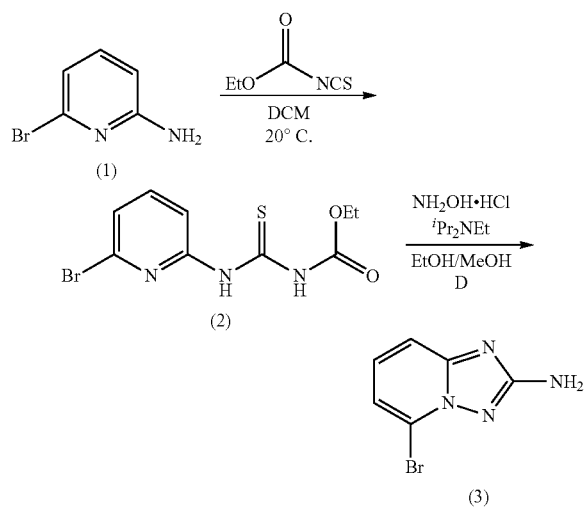

1.1.1.1. 1-(6-Bromo-pyridin-2-yl)-3-carboethoxy-thiourea (2)

To a solution of 2-amino-6-bromopyridine (1) (253.8 g, 1.467 mol) in DCM (2.5 L) cooled to 5° C. was added ethoxycarbonyl isothiocyanate (173.0 mL, 1.467 mol) dropwise over 15 min. The reaction mixture was then allowed to warm to room temp. (20° C.) and stirred for 16 h. Evaporation in vacuo gave a solid which was collected by filtration, thoroughly washed with petrol (3×600 mL) and air-dried to afford (2). The thiourea was used as such in the next step without any purification.

$^1$H (400 MHz, CDCl$_3$) δ 12.03 (1H, br s, NH), 8.81 (1H, d, J=7.8 Hz, H-3), 8.15 (1H, br s, NH), 7.60 (1H, t, J=8.0 Hz, H-4), 7.32 (1H, dd, J 7.7 and 0.6 Hz, H-5), 4.31 (2H, q, J=7.1 Hz, CH$_2$), 1.35 (3H, t, J=7.1 Hz, CH$_3$).

1.1.1.2. 5-Bromo-[1,2,4]triazolo[1,5-a]pyridin-2-ylamine (3)

To a suspension of hydroxylamine hydrochloride (101.8 g, 1.465 mol) in EtOH/MeOH (1:1, 900 mL) was added N,N-diisopropylethylamine (145.3 mL, 0.879 mol) and the mixture was stirred at room temp. (20° C.) for 1 h. 1-(6-Bromo-pyridin-2-yl)-3-carboethoxy-thiourea (2) (89.0 g, 0.293 mol) was then added and the mixture slowly heated to reflux (Note: bleach scrubber was required to quench H$_2$S evolved). After 3 h at reflux, the mixture was allowed to cool and filtered to collect the precipitated solid. Further product was collected by evaporation in vacuo of the filtrate, addition of H$_2$O (250 mL) and filtration. The combined solids were washed successively with H$_2$O (250 mL), EtOH/MeOH (1:1, 250 mL) and Et$_2$O (250 mL) then dried in vacuo to afford the triazolopyridine derivative (3) as a solid. The compound was used as such in the next step without any purification.

$^1$H (400 MHz, DMSO-d$_6$) δ 7.43-7.34 (2H, m, 2× aromatic-H), 7.24 (1H, dd, J 6.8 and 1.8 Hz, aromatic-H), 6.30 (2H, br, NH$_2$); m/z 213/215 (1:1, M+H$^+$, 100%).

1.1.2. Synthesis of 4-[4-(4,4,5,5-Tetramethyl-[1,3,2]dioxaborolan-2-yl)-benzyl]-thiomorpholine-1,1-dioxide (Intermediate 4)

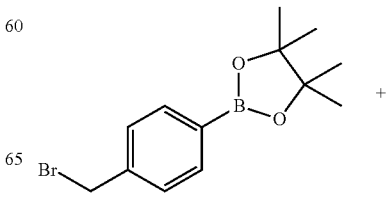

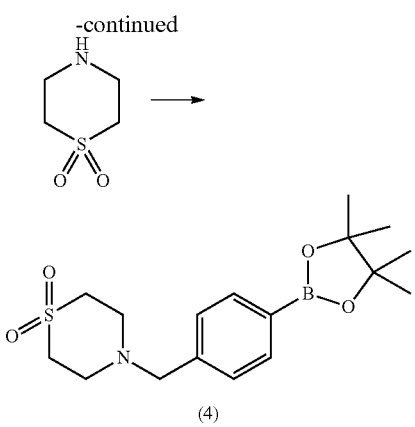

2-(4-Bromomethyl-phenyl)-4,4,5,5-tetramethyl-[1,3,2]dioxaborolane (1 eq) and DIPEA (2 eq) were dissolved in DCM/MeOH (5:1 v:v) under $N_2$ and thiomorpholine 1,1-dioxide (2 eq) was added portion wise. The resulting solution was stirred at room temperature for 16 h. After this time, the reaction was complete. The solvent was evaporated. The compound was extracted with EtOAc and water, washed with brine and dried over anhydrous $MgSO_4$. Organic layers were filtered and evaporated. The final compound was isolated without further purification.

1.1.3. Synthesis of 5-[4-(1,1-Dioxothiomorpholin-4-ylmethyl)-phenyl]-[1,2,4]triazolo[1,5-a]pyridin-2-ylamine (Formula I)

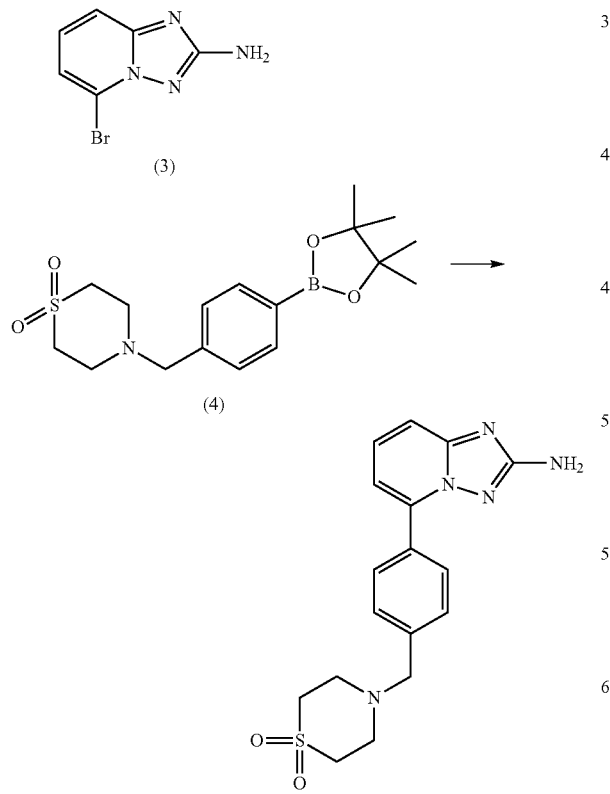

4-[4-(4,4,5,5-Tetramethyl-[1,3,2]dioxaborolan-2-yl)-benzyl]-thiomorpholine-1,1-dioxide (1.1 eq.) was added to a solution of 5-bromo-[1,2,4]triazolo[1,5-a]pyridin-2-ylamine (4:1). $K_2CO_3$ (2 eq.) and $PdCl_2dppf$ (0.03 eq.) were added to the solution. The resulting mixture was then heated in an oil bath at 90° C. for 16 h under $N_2$. Water was added and the solution was extracted with ethyl acetate. The organic layers were dried over anhydrous $MgSO_4$ and evaporated in vacuo. The final compound was obtained after purification by flash chromatography.

$^1$H (400 MHz, $CDCl_3$) δ 7.94-7.92 (d, 2H), 7.52-7.48 (m, 3H), 7.37-7.34 (m, 1H), 7.02-7.00 (m, 1H), 6.00 (d, 2H), 3.76 (d, 2H), 3.15-3.13 (m, 4H), 2.93-2.91 (m, 4H).

m/z 358.2 (M+H$^+$, 100%).

1.2. Route 2

1.2.1. Cyclopropanecarboxylic acid {5-[4-(1,1-dioxo-thiomorpholin-4-ylmethyl)-phenyl]-[1,2,4]triazolo[1,5-a]pyridin-2-yl}-amide (Formula II)

The compound according to Formula II may be synthesized according to the procedure described in WO 2010/149769.

1.2.2. Synthesis of 5-[4-(1,1-Dioxothiomorpholin-4-ylmethyl)-phenyl]-[1,2,4]triazolo[1,5-a]pyridin-2-ylamine (Formula I)

The compound according to Formula I can also be produced by hydrolysis of the compound according to Formula II:

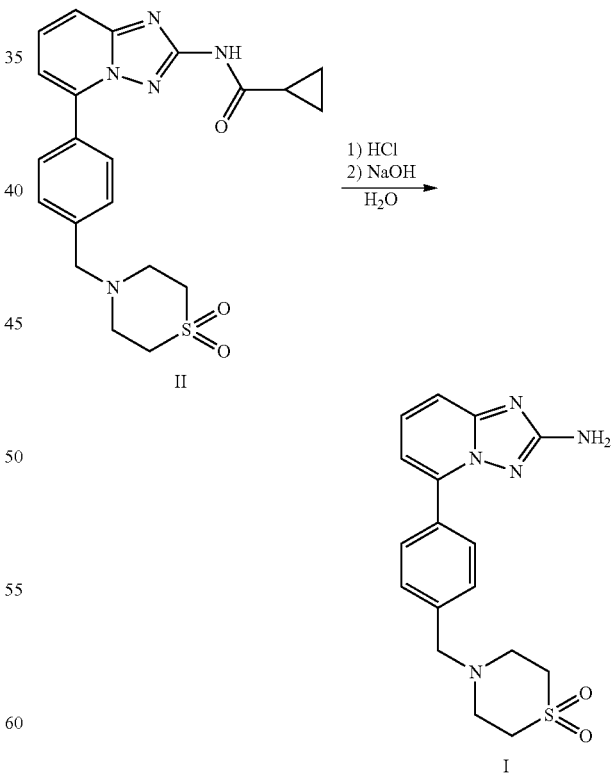

Hydrochloric acid 30% aq (12.06 kg; 3.9 rel. volumes) was added to a slurry of the compound according to Formula II (3.45 kg; 1.0 equiv.) in demineralized water (10.0 kg; 3.0 rel. volumes). Subsequently, a line rinse was performed with demineralized water (3.4 kg; 1.0 rel. volumes). The reaction mixture was heated to 80±5° C. for 14.5 h. After completion of the reaction (conversion ≥99%), the reaction mixture was cooled to 20±5° C. The reaction mixture was diluted with demineralized water (6.8 kg; 2.0 rel. volumes) and sodium hydroxide 33% aq (9.52 kg; 3.7 rel volumes) was dosed at such a rate that the temperature of the reactor contents remained below 35° C. An additional amount of sodium hydroxide 33% aq (2.55 kg; 1.0 rel. volumes) was needed to get the pH≥10. The product was filtered off, washed twice with demineralized water (1.5 rel. volumes) and dried under vacuum for 1 h, thus yielding the crude compound according to Formula I.

The crude compound according to Formula I (5.70 kg) was re-slurried in demineralized water (23.0 kg; 8.5 rel. volumes). Hydrochloric acid 30% aq (1.65 kg; 0.7 rel. volumes) and demineralized water (4.3 kg; 1.6 rel. volumes) were added and the reaction mixture was stirred at 20±5° C. for 45 min. As the compound according to Formula I was not dissolved completely, the reaction mixture was stirred at 45±5° C. for 1 h. The reaction mixture was filtered and the residue was washed with demineralized water (2.0 kg 0.75 rel. volumes). Sodium hydroxide 33% aq (1.12 kg; 0.6 rel volumes) was added to the filtrate. An additional amount of sodium hydroxide 33% aq (1.01 kg) was needed to get the pH≥10. The resulting reaction mixture was stirred at 20±5° C. for about 3 h. The product was filtered off, washed twice with demineralized water (4.1 kg; 1.5 rel. volumes), and twice with methyl tert-butyl ether (MTBE; 3.0 kg; 1.5 rel. volumes) and dried under vacuum for 15.5 h on the filter. The product was further dried in a vacuum oven at 40±5° C. for 202 h, thus affording the desired compound according to Formula I.

Biological Examples

Example 2

In-Vitro Assays 2.1. JAK1 Inhibition Assay 2.1.1. JAK1 Assay polyGT Substrate

Recombinant human JAK1 catalytic domain (amino acids 866-1154; catalog number PV4774) was purchased from Invitrogen. 25 ng of JAK1 was incubated with 6.25 µg polyGT substrate (Sigma catalog number P0275) in kinase reaction buffer (15 mM Hepes pH7.5, 0.01% Tween20, 10 mM $MgCl_2$, 2 µM non-radioactive ATP, 0.25 µCi $^{33}$P-gamma-ATP (Perkin Elmer, catalog number NEG602K001MC) final concentrations) with or without 5 µL containing test compound or vehicle (DMSO, 1% final concentration), in a total volume of 25 µL, in a polypropylene 96-well plate (Greiner, V-bottom). After 75 min at 30° C., reactions were stopped by adding 25 µL/well of 150 mM phosphoric acid. All of the terminated kinase reaction was transferred to prewashed (75 mM phosphoric acid) 96 well filter plates (Perkin Elmer catalog number 6005177) using a cell harvester (Perkin Elmer). Plates were washed 6 times with 300 µL per well of a 75 mM phosphoric acid solution and the bottom of the plates was sealed. 40 µL/well of Microscint-20 was added, the top of the plates was sealed and readout was performed using the Topcount (Perkin Elmer). Kinase activity was calculated by subtracting counts per min (cpm) obtained in the presence of a positive control inhibitor (10 µM staurosporine) from cpm obtained in the presence of vehicle. The ability of a test compound to inhibit this activity was determined as:

> Percentage inhibition=((cpm determined for sample with test compound present−cpm determined for sample with positive control inhibitor) divided by (cpm determined in the presence of vehicle−cpm determined for sample with positive control inhibitor))*100.

Dose dilution series were prepared for the compounds enabling the testing of dose-response effects in the JAK1 assay and the calculation of the $IC_{50}$ for the compound. The compound was tested at a concentration of 20 µM followed by a 1/3 serial dilution, 8 points (20 µM—6.67 µM—2.22 µM—740 nM—247 nM—82 nM—27 nM—9 nM) in a final concentration of 1% DMSO. When compound potency increases, more dilutions were prepared and/or the top concentration is lowered (e.g. 5 µM, 1 µM).

The activity of the compound according to Formula I against JAK1 was determined in accordance with the assay described above, thus returning $IC_{50}$ values of 460.1, 586, 494.3, 758.2, and 432.7 nM (average 546.26 nM).

2.1.2. JAK1 Ulight-JAK1 Peptide Assay

Recombinant human JAK1 (catalytic domain, amino acids 866-1154; catalog number PV4774) was purchased from Invitrogen. 1 ng of JAK1 was incubated with 20 nM Ulight-JAK1(tyr1023) peptide (Perkin Elmer catalog number TRF0121) in kinase reaction buffer (15 mM MOPS pH6.8, 0.01% Brij-35, 5 mM $MgCl_2$, 2 mM DTT, 7 µM ATP) with or without 4 µL containing test compound or vehicle (DMSO, 1% final concentration), in a total volume of 20 µL, in a white 384 Opti plate (Perkin Elmer, catalog number 6007290). After 60 min at room temperature, reactions were stopped by adding 20 µL/well of detection mixture (1× detection buffer (Perkin Elmer, catalog number CR97-100C), 0.5 nM Europium-anti-phosphotyrosine (PT66) (Perkin Elmer, catalog number AD0068), 10 mM EDTA). Readout was performed using the Envision with excitation at 320 nm and measuring emission at 615 nm (Perkin Elmer). Kinase activity was calculated by subtracting relative fluorescence units (RFU) obtained in the presence of a positive control inhibitor (10 µM staurosporine) from RFU obtained in the presence of vehicle. The ability of a test compound to inhibit this activity was determined as:

> Percentage inhibition=((RFU determined for sample with test compound present−RFU determined for sample with positive control inhibitor) divided by (RFU determined in the presence of vehicle−RFU determined for sample with positive control inhibitor))*100.

A dose dilution series was prepared for the compound enabling the testing of dose-response effects in the JAK1 assay and the calculation of the $IC_{50}$ for the compound. The compound was routinely tested at a concentration of 20 µM followed by a 1/5 serial dilution, 10 points in a final concentration of 1% DMSO. When compound potency increases, more dilutions were prepared and/or the top concentration is lowered (e.g. 5 µM, 1 µM). The data were expressed as the average $IC_{50}$ from the assays±standard error of the mean.

The activity of the compound according to Formula I against JAK1 was determined in accordance with the assay described above, thus returning $IC_{50}$ values of 346.8, 714.3, 166.6, 103.3, 187.2, 582.3, 295.3, 241.7, 159.2, 355.3, and 221.6 nM (average=307 nM).

2.1.3. JAK1 Ki Determination Assay

For the determination of Ki, different amounts of compound are mixed with the enzyme and the enzymatic reaction is followed as a function of ATP concentration. The Ki is determined by means of double reciprocal plotting of Km vs compound concentration (Lineweaver-Burk plot). 1 ng of JAK1 (Invitrogen, PV4774) is used in the assay. The substrate is 20 nM Ulight-JAK-1 (Tyr1023) Peptide (Perkin Elmer, TRF0121). The reaction is performed in 15 mM MOPS pH 6.8, 0.01%, Brij-35, 2 mM DTT, 5 mM MgCl2 with varying concentrations of ATP and compound. Phosphorylated substrate is measured using an Europium-labeled anti-phosphotyrosine antibody PT66 (Perkin Elmer, AD0068) as described in 1.1.2. Readout is performed on the envision (Perkin Elmer) with excitation at 320 nm and emission followed at 615 nm and 665 nm.

2.2. JAK2 Inhibition Assay

2.2.1. JAK2 Assay polyGT Substrate

Recombinant human JAK2 catalytic domain (amino acids 808-1132; catalog number PV4210) was purchased from Invitrogen. 0.05 mU of JAK2 was incubated with 2.5 µg polyGT substrate (Sigma catalog number P0275) in kinase reaction buffer (10 mM MOPS pH 7.5, 0.5 mM EDTA, 0.01% Brij-35, 1 mM DTT, 15 mM MgAc, 1 µM non-radioactive ATP, 0.25 µCi $^{33}$P-gamma-ATP (Perkin Elmer, catalog number NEG602K001MC) final concentrations) with or without 5 µL containing test compound or vehicle (DMSO, 1% final concentration), in a total volume of 25 µL, in a polypropylene 96-well plate (Greiner, V-bottom). After 90 min at 30° C., reactions were stopped by adding of 25 µL/well of 150 mM phosphoric acid. All of the terminated kinase reaction was transferred to prewashed (75 mM phosphoric acid) 96 well filter plates (Perkin Elmer catalog number 6005177) using a cell harvester (Perkin Elmer). Plates were washed 6 times with 300 µL per well of a 75 mM phosphoric acid solution and the bottom of the plates was sealed. 40 µL/well of Microscint-20 was added, the top of the plates was sealed and readout was performed using the Topcount (Perkin Elmer). Kinase activity was calculated by subtracting counts per min (cpm) obtained in the presence of a positive control inhibitor (10 µM staurosporine) from cpm obtained in the presence of vehicle. The ability of a test compound to inhibit this activity was determined as:

> Percentage inhibition=((cpm determined for sample with test compound present−cpm determined for sample with positive control inhibitor) divided by (cpm determined in the presence of vehicle−cpm determined for sample with positive control inhibitor))*100.

Dose dilution series were prepared for the compounds enabling the testing of dose-response effects in the JAK2 assay and the calculation of the $IC_{50}$ for each compound. The compound was tested at a concentration of 20 µM followed by a 1/3 serial dilution, 8 points (20 µM—6.67 µM—2.22 µM—740 nM—247 nM—82 nM—27 nM—9 nM) in a final concentration of 1% DMSO. When potency of compound series increases, more dilutions were prepared and/or the top concentration is lowered (e.g. 5 µM, 1 µM).

The activity of the compound according to Formula I against JAK1 was determined in accordance with the assay described above, thus returning $IC_{50}$ values of 566.9, 365.5, 256.4, 915.1, and 1017 nM (average=624 nM).

2.2.2. JAK2 Ulight-JAK1 Peptide Assay

Recombinant human JAK2 (catalytic domain, amino acids 866-1154; catalog number PV4210) was purchased from Invitrogen. 0.0125 mU of JAK2 was incubated with 25 nM Ulight-JAK1(tyr1023) peptide (Perkin Elmer catalog number TRF0121) in kinase reaction buffer (25 mM HEPES pH7.0, 0.01% Triton X-100, 7.5 mM MgCl$_2$, 2 mM DTT, 7.5 µM ATP) with or without 4 µL containing test compound or vehicle (DMSO, 1% final concentration), in a total volume of 20 µL, in a white 384 Opti plate (Perkin Elmer, catalog number 6007290). After 60 min at room temperature, reactions were stopped by adding 20 µL/well of detection mixture (1× detection buffer (Perkin Elmer, catalog number CR97-100C), 0.5 nM Europium-anti-phosphotyrosine (PT66) (Perkin Elmer, catalog number AD0068), 10 mM EDTA). Readout was performed using the Envision with excitation at 320 nm and measuring emission at 615 nm (Perkin Elmer). Kinase activity was calculated by subtracting relative fluorescence units (RFU) obtained in the presence of a positive control inhibitor (10 µM staurosporine) from RFU obtained in the presence of vehicle. The ability of a test compound to inhibit this activity was determined as:

> Percentage inhibition=((RFU determined for sample with test compound present−RFU determined for sample with positive control inhibitor) divided by (RFU determined in the presence of vehicle−RFU determined for sample with positive control inhibitor))*100.

Dose dilution series were prepared for compound enabling the testing of dose-response effects in the JAK2 assay and the calculation of the $IC_{50}$ for the compound. The compound was tested at concentration of 20 µM followed by a 1/5 serial dilution, 10 points in a final concentration of 1% DMSO. When compound potency increases, more dilutions were prepared and/or the top concentration was lowered (e.g. 5 µM, 1 µM). The data were expressed as the average $IC_{50}$ from the assays±standard error of the mean.

The activity of the compound according to Formula I against JAK2 was determined in accordance with the assay described above, thus returning $IC_{50}$ values of 1031, 351.2, 137.5, 367.2, 310.2, 729.2, 151.7, 203.0, 168.0, and 517.0 (average=397 nM).

2.2.3. JAK2 Kd/Ki Determination Assay

2.2.3.1. JAK2 Ki Determination Assay

For the determination of Ki, different amounts of compound are mixed with the enzyme and the enzymatic reaction is followed as a function of ATP concentration. The Ki is determined by means of double reciprocal plotting of Km vs compound concentration (Lineweaver-Burk plot). 0.0125 mU of JAK1 (Invitrogen, PV4210) is used in the assay. The substrate is 25 nM Ulight-JAK-1 (Tyr1023) Peptide (Perkin Elmer, TRF0121). The reaction is performed in 25 mM HEPES pH7.0, 0.01% Triton X-100, 7.5 mM MgCl$_2$, 2 mM DTT with varying concentrations of ATP and compound. Phosphorylated substrate is measured using a Europium-labeled anti-phosphotyrosine antibody PT66 (Perkin Elmer, AD0068) as described in 1.2.2. Readout is performed on the envision (Perkin Elmer) with excitation at 320 nm and emission followed at 615 nm and 665 nm.

2.2.3.2. JAK2 Kd Determination Assay

JAK2 (Invitrogen, PV4210) is used at a final concentration of 2.5 nM. The binding experiment is performed in 50 mM Hepes pH 7.5, 0.01% Brij-35, 10 mM MgCl$_2$, 1 mM EGTA using 25 nM kinase tracer 236 (Invitrogen, PV5592) and 2 nM Europium-anti-GST (Invitrogen, PV5594) with varying compound concentrations. Detection of tracer is performed according to the manufacturer's procedure.

2.2.4. JAK3 Inhibition Assay

Recombinant human JAK3 catalytic domain (amino acids 795-1124; catalog number 08-046) was purchased from Carna Biosciences. 0.5 ng JAK3 protein was incubated with 2.5 µg polyGT substrate (Sigma catalog number P0275) in kinase reaction buffer (25 mM Tris pH 7.5, 0.5 mM EGTA, 10 mM MgCl$_2$, 2.5 mM DTT, 0.5 mM Na$_3$VO$_4$, 5 mM b-glycerolphosphate, 0.01% Triton X-100, 1 µM non-radioactive ATP, 0.25 µCi $^{33}$P-gamma-ATP (Perkin Elmer, catalog number NEG602K001MC) final concentrations) with or without 5 µL containing test compound or vehicle (DMSO, 1% final concentration), in a total volume of 25 µL, in a polypropylene 96-well plate (Greiner, V-bottom). After 45 min at 30° C., reactions were stopped by adding 25 µL/well of 150 mM phosphoric acid. All of the terminated kinase reaction was transferred to prewashed (75 mM phosphoric acid) 96 well filter plates (Perkin Elmer catalog number 6005177) using a cell harvester (Perkin Elmer). Plates were washed 6 times with 300 µL per well of a 75 mM phosphoric acid solution and the bottom of the plates was sealed. 40 µL/well of Microscint-20 was added, the top of the plates was sealed and readout was performed using the Topcount (Perkin Elmer). Kinase activity was calculated by subtracting counts per min (cpm) obtained in the presence of a positive control inhibitor (10 µM staurosporine) from cpm obtained in the presence of vehicle. The ability of a test compound to inhibit this activity was determined as:

Percentage inhibition=((cpm determined for sample with test compound present−cpm determined for sample with positive control inhibitor) divided by (cpm determined in the presence of vehicle−cpm determined for sample with positive control inhibitor))*100.

Dose dilution series were prepared for the compounds enabling the testing of dose-response effects in the JAK3 assay and the calculation of the IC$_{50}$ for the compound. The compound was tested at concentration of 20 µM followed by a 1/5 serial dilution, 10 points in a final concentration of 1% DMSO. When compound increased, more dilutions were prepared and/or the top concentration was lowered (e.g. 5 µM, 1 µM).

The activity of the compound according to Formula I against JAK3 was determined in accordance with the assay described above, thus returning IC$_{50}$ values of 2497, >4000, >4000, >3333, >3333, 3939, >4000, >4000, >4000, 3201, and 3368 (average >3606 nM).

2.2.5. JAK3 Ki Determination Assay

For the determination of Ki, different amounts of compound are mixed with the enzyme and the enzymatic reaction is followed as a function of ATP concentration. The Ki is determined by means of double reciprocal plotting of Km vs compound concentration (Lineweaver-Burk plot). JAK3 (Carna Biosciences, 08-046) is used at a final concentration of 20 ng/mL. The substrate is Poly(Glu,Tyr)sodium salt (4:1), MW 20 000-50 000 (Sigma, P0275) The reaction is performed in 25 mM Tris pH 7.5, 0.01% Triton X-100, 0.5 mM EGTA, 2.5 mM DTT, 0.5 mM Na$_3$VO$_4$, 5 mM b-glycerolphosphate, 10 mM MgCl$_2$ with varying concentrations of ATP and compound and stopped by addition of 150 mM phosphoric acid. Measurement of incorporated phosphate into the substrate polyGT is done by loading the samples on a filter plate (using a harvester, Perkin Elmer) and subsequent washing. Incorporated $^{33}$P in polyGT is measured in a Topcount scintillation counter after addition of scintillation liquid to the filter plates (Perkin Elmer).

2.3. TYK2 Inhibition Assay

Recombinant human TYK2 catalytic domain (amino acids 871-1187; catalog number 08-147) was purchased from Carna biosciences. 4 ng of TYK2 was incubated with 12.5 µg polyGT substrate (Sigma catalog number P0275) in kinase reaction buffer (25 mM Hepes pH 7.2, 50 mM NaCl, 0.5 mM EDTA, 1 mM DTT, 5 mM MnCl$_2$, 10 mM MgCl$_2$, 0.1% Brij-35, 0.1 µM non-radioactive ATP, 0.125 µCi $^{33}$P-gamma-ATP (Perkin Elmer, catalog number NEG602K001MC) final concentrations) with or without 5 µL containing test compound or vehicle (DMSO, 1% final concentration), in a total volume of 25 µL, in a polypropylene 96-well plate (Greiner, V-bottom). After 90 min at 30° C., reactions were stopped by adding 25 µL/well of 150 mM phosphoric acid. All of the terminated kinase reaction was transferred to prewashed (75 mM phosphoric acid) 96 well filter plates (Perkin Elmer catalog number 6005177) using a cell harvester (Perkin Elmer). Plates were washed 6 times with 300 µL per well of a 75 mM phosphoric acid solution and the bottom of the plates was sealed. 40 µL/well of Microscint-20 was added, the top of the plates was sealed and readout was performed using the Topcount (Perkin Elmer). Kinase activity was calculated by subtracting counts per min (cpm) obtained in the presence of a positive control inhibitor (10 µM staurosporine) from cpm obtained in the presence of vehicle. The ability of a test compound to inhibit this activity was determined as:

Percentage inhibition=((cpm determined for sample with test compound present−cpm determined for sample with positive control inhibitor) divided by (cpm determined in the presence of vehicle−cpm determined for sample with positive control inhibitor))*100.

Dose dilution series were prepared for the compounds enabling the testing of dose-response effects in the TYK2 assay and the calculation of the IC$_{50}$ for each compound. Each compound was routinely tested at concentration of 20 µM followed by a 1/3 serial dilution, 8 points (20 µM—6.67 µM—2.22 µM—740 nM—247 nM—82 nM—27 nM—9 nM) in a final concentration of 1% DMSO. When potency of compound series increased, more dilutions were prepared and/or the top concentration was lowered (e.g. 5 µM, 1 µM).

The activity of the compound according to Formula I against TYK2 was determined in accordance with the assay described above, thus returning IC$_{50}$ values of >3333, >3333, >3333, 1973, 2121, 3852, 3819, and 2207 (average >2996 nM).

2.3.1. TYK2 Kd/Ki Determination Assay

2.3.1.1. TYK2 Ki Determination Assay

For the determination of Ki, different amounts of compound are mixed with the enzyme and the enzymatic reaction is followed as a function of ATP concentration. The Ki is determined by means of double reciprocal plotting of Km vs compound concentration (Lineweaver-Burk plot). TYK2 (Carna Biosciences, 08-147) is used at a final concentration of 160 ng/mL. The substrate is Poly(Glu,Tyr)sodium salt (4:1), MW 20 000-50 000 (Sigma, P0275) The reaction is performed in 25 mM Hepes pH 7.2, 50 mM NaCl, 0.5 mM EDTA, 1 mM DTT, 5 mM MnCl$_2$, 10 mM MgCl$_2$, 0.1%

Brij-35 with varying concentrations of ATP and compound and stopped by addition of 150 mM phosphoric acid. Measurement of incorporated phosphate into the substrate polyGT is done by loading the samples on a filter plate (using a harvester, Perkin Elmer) and subsequent washing. Incorporated $^{33}$P in polyGT is measured in a Topcount scintillation counter after addition of scintillation liquid to the filter plates (Perkin Elmer).

2.3.1.2. TYK2 Kd Determination Assay

TYK2 (Carna Biosciences, 08-147) is used at a final concentration of 50 nM. The binding experiment is performed in 50 mM Hepes pH 7.5, 0.01% Brij-35, 10 mM $MgCl_2$, 1 mM EGTA using 15 nM kinase tracer 236 (Invitrogen, PV5592) and 10 nM Europium-anti-GST (Invitrogen, PV5594) with varying compound concentrations. Detection of tracer is performed according to the manufacturers' procedure.

Example 3

Cellular Assays

3.1. JAK-STAT Signalling Assay

HeLa cells were maintained in Dulbecco's Modified Eagle's Medium (DMEM) containing 10% heat inactivated fetal calf serum, 100 U/mL penicillin and 100 µg/mL streptomycin. HeLa cells were used at 70% confluence for transfection. 20,000 cells in 87 µL cell culture medium were transiently transfected with 40 ng pSTAT1(2)-luciferase reporter (Panomics), 8 ng of LacZ reporter as internal control reporter and 52 ng of pBSK using 0.32 µL Jet-PEI (Polyplus) as transfection reagent per well in 96-well plate format. After overnight incubation at 37° C., 5% $CO_2$, transfection medium was removed. 81 µL of DMEM+1.5% heat inactivated fetal calf serum was added. 9 µL compound at 10× concentration was added for 60 min and then 10 µL of human OSM (Peprotech) at 33 ng/mL final concentration.

The compound was tested in duplicate starting from 20 µM followed by a 1/3 serial dilution, 8 doses in total (20 µM—6.6 µM—2.2 µM—740 nM—250 nM—82 nM—27 nM—9 nM) in a final concentration of 0.2% DMSO.

After overnight incubation at 37° C., 5% $CO_2$ cells were lysed by adding 100 µL lysis buffer/well (PBS, 0.9 mM $CaCl_2$, 0.5 mM $MgCl_2$, 10% Trehalose, 0.05% Tergitol NP9, 0.3% BSA).

40 µL of cell lysate was used to read β-galactosidase activity by adding 180 µL β-Gal solution (30 µL ONPG 4 mg/mL+ 150 µL β-Galactosidase buffer (0.06 M $Na_2HPO_4$, 0.04 M $NaH_2PO_4$, 1 mM $MgCl_2$)) for 20 min. The reaction was stopped by addition of 50 µL $Na_2CO_3$ 1 M. Absorbance was read at 405 nm.

Luciferase activity was measured using 40 µL cell lysate plus 40 µL of Steadylite® as described by the manufacturer (Perkin Elmer), on the Envision (Perkin Elmer).

Omitting OSM was used as a positive control (100% inhibition). As negative control 0.5% DMSO (0% inhibition) was used. The positive and negative controls were used to calculate z' and 'percent inhibition' (PIN) values.

Percentage inhibition=((fluorescence determined in the presence of vehicle–fluorescence determined for sample with test compound present) divided by (fluorescence determined in the presence of vehicle–fluorescence determined for sample without trigger))*100.

PIN values were plotted for compounds tested in dose-response and $EC_{50}$ values were derived.

The activity of the compound according to Formula I against JAK-STAT was determined in accordance with the assay described above, thus returning an $IC_{50}$ value of Non active, >6670, >6670, 8943 (average >7427 nM).

3.2. OSM/IL-1β Signaling Assay

OSM and IL-1β are shown to synergistically upregulate MMP13 levels in the human chondrosarcoma cell line SW1353. The cells are seeded in 96 well plates at 15,000 cells/well in a volume of 120 µL DMEM (Invitrogen) containing 10% (v/v) FBS and 1% penicillin/streptomycin (Invitrogen) incubated at 37° C. 5% $CO_2$. Cells are preincubated with 15 µL of compound in M199 medium with 2% DMSO 1 h before triggering with 15 µL OSM and IL-1β to reach 25 ng/mL OSM and 1 ng/mL IL-1β, and MMP13 levels are measured in conditioned medium 48 h after triggering. MMP13 activity is measured using an antibody capture activity assay. For this purpose, 384 well plates (NUNC, 460518, MaxiSorb black) are coated with 35 µL of a 1.5 µg/mL anti-human MMP13 antibody (R&D Systems, MAB511) solution for 24 h at 4° C. After washing the wells 2 times with PBS+ 0.05% Tween, the remaining binding sites are blocked with 100 µL 5% non-fat dry milk (Santa Cruz, sc-2325, Blotto) in PBS for 24 h at 4° C. Next, the wells are washed twice with PBS+0.05% Tween and 35 µL of 1/10 dilution of culture supernatant containing MMP13 in 100-fold diluted blocking buffer is added and incubated for 4 h at room temperature. Next the wells are washed twice with PBS+0.05% Tween followed by MMP13 activation by addition of 35 µL of a 1.5 mM 4-Aminophenylmercuric acetate (APMA) (Sigma, A9563) solution and incubation at 37° C. for 1 h. The wells are washed again with PBS+0.05% Tween and 35 µL MMP13 substrate (Biomol, P-126, OmniMMP fluorogenic substrate) is added. After incubation for 24 h at 37° C. fluorescence of the converted substrate is measured in a Perkin Elmer Wallac EnVision 2102 Multilabel Reader (wavelength excitation: 320 nm, wavelength emission: 405 nm).

Percentage inhibition=((fluorescence determined in the presence of vehicle–fluorescence determined for sample with test compound present) divided by (fluorescence determined in the presence of vehicle–fluorescence determined for sample without trigger))*100.

3.3. PBL Proliferation Assay

Human peripheral blood lymphocytes (PBL) are stimulated with IL-2 and proliferation is measured using a BrdU incorporation assay. The PBL are first stimulated for 72 h with PHA to induce IL-2 receptor, then they are fasted for 24 h to stop cell proliferation followed by IL-2 stimulation for another 72 h (including 24 hr BrdU labeling). Cells are pre-incubated with test compounds 1 hr before IL-2 addition. Cells are cultured in RPMI 1640 containing 10% (v/v) FBS.

3.4. Human Whole Blood Assay (hWBA)

3.4.1. Protocol 1

3.4.1.1. IL-6 Stimulation Protocol

A flow cytometry analysis was performed to establish JAK1 over JAK2 compound selectivity ex vivo using human whole blood. Therefore, blood is taken from human volunteers who gave informed consent. Blood is then equilibrated for 30 min at 37° C. under gentle rocking, then aliquoted in Eppendorf tubes. Compound is added at different concentrations and incubated at 37° C. for 30 min under gentle rocking and subsequently stimulated for 20 min at 37° C. under gentle rocking with interleukin 6 (IL-6) for JAK1-dependent pathway stimulation or GM-CSF for JAK2-dependent pathway stimulation. Phospho-STAT1 and phospho-STAT5 are then evaluated using FACS analysis.

3.4.1.1.1. Phospho-STAT1 Assays

3.4.1.1.1.1. Preparation of Reagents

The 5× Lyse/Fix buffer (BD PhosFlow, Cat. no 558049) was diluted 5-fold with distilled water and pre-warmed at 37° C. The remaining diluted Lyse/Fix buffer was discarded.

10 μg rhIL-6 (R&D Systems, Cat no 206-IL) was dissolved in 1 mL of PBS 0.1% BSA to obtain a 10 μg/mL stock solution. The stock solution was aliquoted and stored at −80° C.

A 3-fold dilution series of the compound was prepared in DMSO (10 mM stock solution). Control-treated samples received DMSO instead of compound. All samples were incubated with a 1% final DMSO concentration.

3.4.1.1.1.2. Incubation of Blood with Compound and Stimulation with IL-6

Human blood is collected in heparinized tubes. The blood is divided in aliquots of 148.5 μL. Then, 1.5 μL of the test compound dilution is added to each blood aliquot and the blood samples are incubated for 30 min at 37° C. under gentle rocking. One and a half microliter of 10-fold diluted IL-6 stock solution is added to the blood samples (final concentration 10 ng/mL) and samples are incubated at 37° C. for 20 min under gentle rocking.

3.4.1.1.1.3. White Blood Cell Preparation

At the end of the stimulation period, 3 mL of 1× pre-warmed Lyse/Fix buffer is immediately added to the blood samples, vortexed briefly and incubated for 15 min at 37° C. in a water bath in order to lyse red blood cells and fix leukocytes.

Tubes are centrifuged for 5 min at 400×g at 4° C. The cell pellet is washed with 3 mL of cold 1×PBS, and after centrifugation the cell pellet is resuspended in 100 μL of ice-cold 1×PBS and 900 μL ice-cold 100% methanol is added. Cells are then incubated at 4° C. for 30 min for permeabilization.

Permeabilized cells are then washed with 1×PBS containing 3% BSA and finally resuspended in 80 μL of 1×PBX containing 3% BSA.

3.4.1.1.1.4. Cell Labeling with Anti Phospho-STAT1 and Anti-CD4 Antibodies

20 μL of PE mouse anti-STAT1 (pY701) or PE mouse IgG2aκ isotype control antibody (BD Biosciences, Cat. no 612564 and 559319, respectively) and FITC-conjugated anti-CD4 antibody or control FITC-conjugated isotype antibody were added and mixed, then incubated for 30 min at 4° C., in the dark.

Cells were then washed once with 1×PBS and analyzed on a FACSCanto II flow cytometer (BD Biosciences).

3.4.1.1.1.5. Fluorescence Analysis on FACSCanto II 50,000 total events are counted and Phospho-STAT1 positive cells are measured after gating on $CD4^+$ cells, in the lymphocyte gate. Data are analyzed using the FACSDiva software and the percentage of inhibition of IL-6 stimulation calculated from the percentage of positive cells for phospho-STAT1 on CD4+ cells.

3.4.1.1.2. Phospho-STAT5 Assay

3.4.1.1.2.1. Preparation of Reagents

The 5× Lyse/Fix buffer (BD PhosFlow, Cat. no 558049) was diluted 5-fold with distilled water and pre-warmed at 37° C. Remaining diluted Lyse/Fix buffer was discarded.

10 μg rhGM-CSF (AbCys S. A., Cat no P300-03) was dissolved in 100 μL of PBS 0.1% BSA to obtain a 100 μg/mL stock solution. The stock solution was stored aliquoted at −80° C.

A 3-fold dilution series of the compound was prepared in DMSO (10 mM stock solution). Control-treated samples receive DMSO without the test compound. All samples were incubated with a 1% final DMSO concentration.

3.4.1.1.2.2. Incubation of Blood with Compound and Stimulation with GM-CSF

Human blood was collected in heparinized tubes. The blood was divided in aliquots of 148.5 μL. Then, 1.5 μL of compound dilution was added to each aliquot and the blood samples were incubated for 30 min at 37° C. under gentle rocking. A 5.000-fold dilution of the GM-CSF stock solution (1.5 μL) was added to the blood samples (final concentration 20 pg/mL) and samples were incubated at 37° C. for 20 min under gentle rocking.

3.4.1.1.2.3. White Blood Cell Preparation

At the end of the stimulation period, 3 mL of 1× pre-warmed Lyse/Fix buffer was immediately added to the blood samples, vortexed briefly and incubated for 15 min at 37° C. in a water bath in order to lyse red blood cells and fix leukocytes Tubes were centrifuged for 5 min at 400×g at 4° C. The cell pellet was washed with 3 mL of cold 1×PBS, and after centrifugation the cell pellet was resuspended in 100 μL of ice-cold 1×PBS and 900 μL ice-cold 100% methanol was added. Cells were then incubated at 4° C. for 30 min for permeabilization.

3.4.1.1.2.4. Cell Labeling with Anti Phospho-STAT5 and Anti-CD33 Antibodies 20 μL of PE mouse anti-STAT5 (pY694) or PE mouse IgG1κ isotype control antibody (BD Biosciences, Cat. no 612567 and 554680, respectively) and APC mouse anti CD33 antibody (BD Biosciences #345800) or control APC mouse IgG1 isotype antibody (BD Biosciences #345818) were added, mixed then incubated for 30 min at 4° C., in the dark.

Cells were then washed once with 1×PBS and analyzed on a FACSCanto II flow cytometer (BD Biosciences).

3.4.1.1.2.5. Fluorescence Analysis on FACSCanto II 50,000 total events were counted and Phospho-STAT5 positive cells were measured after gating on $CD33^+$ cells.

Data were analyzed using the FACSDiva software and correspond to the percentage of inhibition of GM-CSF stimulation calculated from the percentage of positive cells for phosphor-STAT5 on CD33+ cells.

3.4.2. Protocol 2

3.4.2.1. Stimulation Protocol

A flow cytometry analysis was performed to establish JAK1 over JAK2 compound selectivity ex vivo using human whole blood. Therefore, blood is taken from human volunteers who gave informed consent. Blood is then equilibrated for 30 min at 37° C. under gentle rocking, then aliquoted in Eppendorf tubes. Compound is added at different concentrations and incubated at 37° C. for 30 min under gentle rocking and subsequently stimulated for 20 min at 37° C. under gentle rocking with interleukin 6 (IL-6) for JAK1-dependent pathway stimulation, Interferon alpha (IFNα) for JAK1/TYK2 pathway stimulation, interleukin 2 (IL-2) for JAK1/JAK3 pathway stimulation or GM-CSF for JAK2-dependent pathway stimulation. Phospho-STAT1 (for IL-6- and IFNα-stimulated cells) and phospho-STAT5 (for IL-2- and GM-CSF-stimulated cells) levels are then evaluated using FACS analysis.

3.4.2.2. Phospho-STAT Assays

3.4.2.2.1. Preparation of Reagents

The 5× Lyse/Fix buffer (BD PhosFlow, Cat. no 558049) was diluted 5-fold with distilled water and pre-warmed at 37° C. The remaining diluted Lyse/Fix buffer was discarded.

10 μg rhIL-6 (R&D Systems, Cat no 206-IL) was dissolved in 1 mL of PBS+0.1% BSA to obtain a 10 μg/mL stock solution. The stock solution was aliquoted and stored at −80° C.

10 μg rhIL-2 (R&D Systems, Cat no 202-IL) was dissolved in 1 mL of PBS+0.1% BSA to obtain a 10 μg/mL stock solution. The stock solution was aliquoted and stored at −80° C.

5 μg rhGM-CSF (AbCys S. A., Cat no P300-03) was dissolved in 12.5 mL of PBS+0.1% BSA to obtain a 400 ng/mL stock solution. The stock solution was stored aliquoted at −80° C.

A 3-fold dilution series of the compound was prepared in DMSO (10 mM stock solution). Control-treated samples received DMSO instead of compound. All samples were incubated with a 1% final DMSO concentration.

3.4.2.2.2. Incubation of Blood with Compound and Stimulation with Triggers Human blood was collected in heparinized tubes. The blood was divided in aliquots of 148.5 μL. Then, 1.5 μL of the test compound dilution was added to each blood aliquot and the blood samples were incubated for 30 min at 37° C. under gentle rocking. One and a half microliter of 10-fold diluted IL-6 stock solution, 1.5 μL of uIFNα (PBL Biomedical, Cat no 11200-1) stock solution, 1.5 μL of 25-fold diluted IL-2 stock solution or 1.5 μL of 200-fold dilution of the GM-CSF stock solution was added to the blood samples and samples were incubated at 37° C. for 20 min under gentle rocking.

3.4.2.2.3. White Blood Cell Preparation

At the end of the stimulation period, 3 mL of 1× pre-warmed Lyse/Fix buffer was immediately added to the blood samples, vortexed briefly and incubated for 15 min at 37° C. in a water bath in order to lyse red blood cells and fix leukocytes.

Tubes were centrifuged for 5 min at 400×g at 4° C. The cell pellet was washed with 3 mL of cold 1×PBS, and after centrifugation the cell pellet was resuspended in 100 μL of ice-cold 1×PBS and 900 μL ice-cold 100% methanol is added. Cells were then incubated at 4° C. for 30 min for permeabilization.

Permeabilized cells were then washed with 1×PBS containing 3% BSA and finally resuspended in 80 μL of 1×PBX containing 3% BSA.

3.4.2.2.4. Cell Labeling

20 μL of PE mouse anti-STAT1 (pY701) or PE mouse IgG2aκ isotype control antibody (BD Biosciences, Cat. no 612564 and 559319, respectively) and APC-conjugated anti-CD4 antibody or control APC-conjugated isotype antibody (BD Biosciences, Cat. no 555349 and 555751, respectively) were added to IL-6- and IFNα-stimulated tubes and mixed, then incubated for 20 min at 4° C., in the dark.

20 μL of PE mouse anti-STAT5 (pY694) or PE mouse IgG1κ isotype control antibody (BD Biosciences, Cat. no 612567 and 554680, respectively) and APC-conjugated anti-CD4 antibody or control APC-conjugated isotype antibody (BD Biosciences, Cat. no 555349 and 555751, respectively) were added to IL-2-stimulated tubes, mixed then incubated for 20 min at 4° C., in the dark.

20 μL of PE mouse anti-STAT5 (pY694) or PE mouse IgG1κ isotype control antibody (BD Biosciences, Cat. no 612567 and 554680, respectively) and APC mouse anti CD33 antibody (BD Biosciences #345800) or control APC mouse IgG1 isotype antibody (BD Biosciences Cat. no 345818) were added to GM-CSF-stimulated tubes, mixed then incubated for 20 min at 4° C., in the dark.

Cells were then washed once with 1×PBS and analyzed on a FACSCanto II flow cytometer (BD Biosciences).

3.4.2.2.5. Fluorescence Analysis on FACSCanto II 50,000 total events were counted and Phospho-STAT1 positive cells were measured after gating on CD4+ cells, in the lymphocyte gate for IL-6– and IFNα-stimulated cells. Phospho-STAT5 positive cells were measured after gating on CD4+ cells, in the lymphocyte gate for IL-2-stimulated cells. Phospho-STAT5 positive cells were measured after gating on CD33+ cells. Data are analyzed using the FACSDiva software and the percentage of inhibition of IL-6 or IFNα stimulation calculated is from the percentage of positive cells for phospho-STAT1 on CD4+ cells. For the IL-2 stimulated cells, data were analyzed using the FACSDiva software and the percentage of inhibition of IL-2 stimulation was calculated from the percentage of positive cells for phospho-STAT1 on CD4+ cells. For the GM-CSF stimulated cells, the percentage of inhibition of GM-CSF stimulation was calculated from the percentage of positive cells for phosphor-STAT5 on CD33+ cells.

3.4.3. Results

When submitted to these protocols, the compound according to Formula I returned a mean $IC_{50}$ of 11.9 µM on IL-6-induced STAT1 phosphorylation, on 6 different donors. On the IFNα-induced STAT1 phosphorylation, the mean $IC_{50}$ was evaluated to be 15.4 µM on 6 different donors. On the IL-2-induced STAT5 phosphorylation, the mean $IC_{50}$ was evaluated to be 19.6 µM in 5 different donors. On the GM-CSF-induced STAT5 phosphorylation, the mean $IC_{50}$ was evaluated to be over 100 µM in 7 different donors.

Example 4

In Vivo Models

4.1. CIA Model 1

4.1.1. Materials

Complete Freund's adjuvant (CFA) and Incomplete Freund's adjuvant (IFA) were purchased from Difco. Bovine collagen type II (CII), lipopolysaccharide (LPS), and Enbrel® was obtained from Chondrex (Isle d'Abeau, France); Sigma (P4252, L'Isle d'Abeau, France), Whyett (25 mg injectable syringe, France), Whyett (25 mg injectable syringe, France) Acros Organics (Palo Alto, Calif.), respectively. All other reagents used were of reagent grade and all solvents were of analytical grade.

4.1.2. Animals

Dark Agouti rats (male, 7-8 weeks old) were obtained from Harlan Laboratories (Melderslo, Netherlands). Rats were kept on a 12 hr light/dark cycle (0700-1900). Temperature was maintained at 22° C., and food and water were provided ad libitum.

4.1.3. Collagen Induced Arthritis (CIA)

One day before the experiment, CII solution (2 mg/mL) was prepared with 0.05 M acetic acid and stored at 4° C. Just before the immunization, equal volumes of adjuvant (IFA) and CII were mixed by a homogenizer in a pre-cooled glass bottle in an ice water bath. Extra adjuvant and prolonged homogenization may be required if an emulsion was not formed. 0.2 mL of the emulsion was injected intradermally at the base of the tail of each rat on day 1, a second booster intradermal injection (CII solution at 2 mg/mL in CFA 0.1 mL saline) was performed on day 9. This immunization method was modified from published methods (Sims et al, 2004; Jou et al., 2005).

4.1.4. Study Design

The therapeutic effects of the compounds were tested in the rat CIA model. Rats were randomly divided into equal groups and each group contained 10 rats. All rats were immunized on day 1 and boosted on day 9. Therapeutic dosing lasts from day 16 to day 30. The negative control group was treated with vehicle (MC 0.5%) and the positive control group with Enbrel® (10 mg/kg, 3× week, s.c.). A compound of interest was typically tested at 3 doses, e.g. 6, 10, 60 mg/kg, q.d., p.o.

4.1.5. Clinical Assessment of Arthritis

Arthritis was scored according to the method of Khachigian 2006, Lin et al 2007 and Nishida et al. 2004). The swelling of each of the four paws was ranked with the arthritic score as follows: 0—no symptoms; 1—mild, but definite redness and swelling of one type of joint such as the ankle or wrist, or apparent redness and swelling limited to individual digits, regardless of the number of affected digits; 2—moderate redness and swelling of two or more types of joints; 3—severe redness and swelling of the entire paw including digits; 4—maximally inflamed limb with involvement of multiple joints (maximum cumulative clinical arthritis score 16 per animal) (Nishida et al., 2004).

To permit the meta-analysis of multiple studies the clinical score values were normalised as follows:

AUC of clinical score (AUC score): The area under the curve (AUC) from day 1 to day 14 was calculated for each individual rat. The AUC of each animal was divided by the average AUC obtained for the vehicle in the study from which the data on that animal was obtained and multiplied by 100 (i.e. the AUC was expressed as a percentage of the average vehicle AUC per study).

Clinical score increase from day 1 to day 14 (End point score): The clinical score difference for each animal was divided by the average clinical score difference obtained for the vehicle in the study from which the data on that animal was obtained and multiplied by 100 (i.e. the difference was expressed as a percentage of the average clinical score difference for the vehicle per study).

4.1.6. Change in Body Weight (%) after Onset of Arthritis

Clinically, body weight loss was associated with arthritis (Shelton et al., 2005; Argiles et al., 1998; Rall, 2004; Walsmith et al., 2004). Hence, changes in body weight after onset of arthritis can be used as a non-specific endpoint to evaluate the effect of therapeutics in the rat model. The change in body weight (%) after onset of arthritis was calculated as follows:

$$\text{Mice:} \frac{\text{Body Weight}_{(\text{week } 6)} - \text{Body Weight}_{(\text{week } 5)}}{\text{Body Weight}_{(\text{week } 5)}} \times 100\%$$

$$\text{Rats:} \frac{\text{Body Weight}_{(\text{week } 4)} - \text{Body Weight}_{(\text{week } 3)}}{\text{Body Weight}_{(\text{week } 3)}} \times 100\%$$

4.1.7. Radiology

X-ray photos were taken of the hind paws of each individual animal. A random blind identity number was assigned to each of the photos, and the severity of bone erosion was ranked by two independent scorers with the radiological Larsen's score system as follows: 0—normal with intact bony outlines and normal joint space; 1—slight abnormality with any one or two of the exterior metatarsal bones showing slight bone erosion; 2—definite early abnormality with any three to five of the exterior metatarsal bones showing bone erosion; 3—medium destructive abnormality with all the exterior metatarsal bones as well as any one or two of the interior metatarsal bones showing definite bone erosions; 4—severe destructive abnormality with all the metatarsal bones showing definite bone erosion and at least one of the inner metatarsal joints completely eroded leaving some bony joint outlines partly preserved; 5—mutilating abnormality without bony outlines. This scoring system was a modification from Salvemini et al., 2001; Bush et al., 2002; Sims et al., 2004; Jou et al., 2005.

4.1.8. Histology

After radiological analysis, the hind paws of mice were fixed in 10% phosphate-buffered formalin (pH 7.4), decalcified with rapid bone decalcifiant for fine histology (Laboratories Eurobio) and embedded in paraffin. To ensure extensive evaluation of the arthritic joints, at least four serial sections (5 µm thick) were cut and each series of sections were 100 µm in between. The sections were stained with hematoxylin and eosin (H&E). Histologic examinations for synovial inflammation and bone and cartilage damage were performed using a double blind protocol. In each paw, four parameters were assessed using a four-point scale. The parameters were cell infiltration, pannus severity, cartilage erosion and bone erosion. Scoring was performed accordingly, as follows: 1-normal, 2-mild, 3-moderate, 4-marked. The four scores were summed together and represented as an additional score, namely the 'RA total score'.

4.1.9. Micro-Computed Tomography (uCT) Analysis of Calcaneus (Heel Bone)

Bone degradation observed in RA occurs especially at the cortical bone and can be revealed by µCT analysis (Sims N A et al., Arthritis Rheum. 50 (2004) 2338-2346: Targeting osteoclasts with zoledronic acid prevents bone destruction in collagen-induced arthritis; Oste L et al., ECTC Montreal 2007: A high throughput method of measuring bone architectural disturbance in a murine CIA model by micro-CT morphometry). After scanning and 3D volume reconstruction of the calcaneus bone, bone degradation was measured as the number of discrete objects present per slide, isolated in silico perpendicular to the longitudinal axis of the bone. The more the bone was degraded, the more discrete objects were measured. 1000 slices, evenly distributed along the calcaneus (spaced by about 10.8 µm), were analyzed.

4.1.10. Steady State PK

At day 7 or 11, blood samples were collected at the retro-orbital sinus with lithium heparin as anti-coagulant at the following time points: predose, 1, 3 and 6 hrs. Whole blood samples were centrifuged and the resulting plasma samples were stored at −20° C. pending analysis. Plasma concentrations of each test compound were determined by an LC-MS/MS method in which the mass spectrometer was operated in positive electrospray mode. Pharmacokinetic parameters were calculated using Winnonlin® (Pharsight®, United States) and it was assumed that the predose plasma levels were equal to the 24 h plasma levels.

4.1.11. Results

The compound according to Formula I exhibited statistically significant improvements in the normalized clinical score values (calculated as AUC or as the difference from day 1 to day 14) at a dose of 60 mg/kg as shown on FIG. 1 and Table I.

TABLE I

Rat CIA Clinical Score after treatment with the compounds disclosed herein.

| Day | 18 | 19 | 20 | 21 | 24 | 25 | 26 | 27 | 28 |
|---|---|---|---|---|---|---|---|---|---|
| Vehicle | 2.9 | 3.8 | 6.0 | 6.0 | 6.4 | 6.3 | 6.3 | 6.3 | 6.4 |
| Formula II (6 mg/kg) | 3.0 | 3.6 | 4.2 | 5.1 | 5.2 | 5.1 | 4.9 | 5.2 | 5.4 |
| Formula I (60 mg/kg) | 2.9 | 4.4 | 5.0 | 3.9 | 4.5 | 4.3 | 3.8 | 3.7 | 3.3 |
| Formula II (6 mg/kg) + Formula I (60 mg/kg) | 3.0 | 3.6 | 4.4 | 4.5 | 4.5 | 4.1 | 3.9 | 4.3 | 3.6 |

4.2. CIA Model 2

4.2.1. Animals

Female Lewis rats (n=76) that weighed 165-194 grams (mean approx. 178 g) on arthritis day 0 were obtained from Charles River Laboratories, Inc., Wilmington, Mass., (ref#393739). Animals were identified by a distinct number at the base of the tail delineating group and animal number.

Upon arrival, animals were housed 4/cage in shoe-box polycarbonate cages and acclimated for 8 days prior to being immunized with type II collagen. No concurrent medications were given.

During the acclimation and study periods, animals were housed in a laboratory environment with temperatures ranging 19-25° F. and relative humidity of 30%-70%. Automatic timers provided 12 h of light and 12 h of dark Animals were allowed access ad libitum to food and water.

4.2.2. Collagen Induced Arthritis (CIA)

4.2.2.1. Preparation

Acclimated female Lewis rats were anesthetized with Isoflurane and receive subcutaneous/intradermal (SC/ID) injections with 300 µL of Freund's Incomplete Adjuvant (Difco, Detroit, Mich.) containing 2 mg/mL bovine type II collagen (Elastin Products, Owensville, Mo.) at the base of the tail and 2 sites on the back on day −9 and on day −3.

Collagen was prepared by making a 4 mg/mL solution in 0.01N Acetic acid. Equal volumes of collagen and Freund's incomplete adjuvant, were emulsified by hand mixing until a bead of this material holds its form when placed in water. Each animal received 300 µL of the mixture on each occasion divided over 3 subcutaneous sites on back.

4.2.2.2. Study

On study day 1, onset of arthritis occurred and animals were randomized into treatment groups. After randomization, all cages were labelled with protocol number, group number, and animal numbers. Randomization into each group was done after ankle joint swelling was obviously established and there was good evidence of bilateral disease.

Animals with established type II collagen arthritis were treated daily (QD) by the oral (PO) route for 13 days with vehicle (methylcellulose 0.5% (w/v)), or with active compound(s) prepared in methylcellulose, 0.5% (w/v). Oral dosing was initiated on arthritis day 1 and continued daily (QD at 24 h intervals) through day 13. Animals were terminated on arthritis day 14.

4.2.2.3. Clinical Assessment of Arthritis

The severity of the arthritis was evaluated by measuring the diameter of both ankles on the animals. Caliper measurements of ankles were taken every day beginning on day 0, with a Digitrix II micrometer (Fowler & NSK). Baseline measurements were taken using one ankle with values rounded to one-thousandth of an inch. Measurements were confirmed as clinically normal (0.260-0.264 in) by comparison with historical values for rats based on a range of body weights. Baseline measurements were then applied to both ankles, and these values remain with the animal so long as the ankle was clinically normal with good definition of all the ankle bones and no evidence of inflammation. Animals were terminated on day 14.

4.2.2.4. Compounds, Dosage and Results

The compounds were tested individually and in combination at various doses, which are listed in Table II below.

TABLE II

Compounds and dose tested in the CIA second model

| Compounds | Dose | Group |
|---|---|---|
| control PO, QD | — | A |
| Vehicle (MC, 0.5%, w/v) | 5 mL/kg | B |
| Formula II | 1 mg/kg | C |
|  | 3 mg/kg | D |
|  | 10 mg/kg(*) | E |
|  | 30 mg/kg(*) | F |
| Formula I | 25 mg/kg(*) | G |
|  | 50 mg/kg(*) | H |
| Formula II + Formula I | 3 mg/kg (Formula II) + 25 mg/kg (Formula I),(*) | I |

(* = $p \leq 0.05$ ANOVA to vehicle control)

4.2.2.5. Conclusion

Figure 2:
FIG. 2: Shows the evolution of ankle diameter in the rat CIA model after treatment with the compounds disclosed herein.

Ankle diameter measurements indicate that administering the combination of the compound according to Formula I (25 mg/kg) and Formula II (3 mg/kg) provides a stronger effect than the effect obtained with the compound according to Formula I (25 mg/kg) alone or the compound according to Formula II (3 mg/kg) alone, as shown on FIG. 2 and Table III below.

TABLE III

Evolution of ankle diameter (inches) in the rat CIA model after treatment with the compounds disclosed herein.

| Days | Groups | | | | | | | |
|---|---|---|---|---|---|---|---|---|
|  | A | B | C | D | E | F | G | H |
| 0 | 0.2635 | 0.2628 | 0.2625 | 0.2623 | 0.2626 | 0.2620 | 0.2629 | 0.2624 |
| 1 | 0.2635 | 0.2717 | 0.2716 | 0.2718 | 0.2718 | 0.2718 | 0.2717 | 0.2718 |
| 2 | 0.2635 | 0.2780 | 0.2755 | 0.2755 | 0.2744 | 0.2679 | 0.2747 | 0.2705 |
| 3 | 0.2635 | 0.2865 | 0.2869 | 0.2869 | 0.2808 | 0.2683 | 0.2826 | 0.2814 |
| 4 | 0.2635 | 0.2980 | 0.2990 | 0.2957 | 0.2850 | 0.2708 | 0.2892 | 0.2886 |
| 5 | 0.2635 | 0.3109 | 0.3106 | 0.3058 | 0.2921 | 0.2698 | 0.2973 | 0.2970 |
| 6 | 0.2635 | 0.3246 | 0.3231 | 0.3168 | 0.3000 | 0.2696 | 0.3064 | 0.3061 |
| 7 | 0.2635 | 0.3290 | 0.3296 | 0.3205 | 0.3031 | 0.2706 | 0.3108 | 0.3110 |
| 8 | 0.2635 | 0.3301 | 0.3291 | 0.3259 | 0.3108 | 0.2741 | 0.3150 | 0.3160 |
| 9 | 0.2635 | 0.3260 | 0.3268 | 0.3216 | 0.3119 | 0.2721 | 0.3089 | 0.3085 |
| 10 | 0.2635 | 0.3227 | 0.3270 | 0.3197 | 0.3122 | 0.2706 | 0.3046 | 0.3032 |
| 11 | 0.2635 | 0.3187 | 0.3185 | 0.3156 | 0.3090 | 0.2711 | 0.3025 | 0.3041 |
| 12 | 0.2635 | 0.3186 | 0.3178 | 0.3165 | 0.3070 | 0.2685 | 0.3006 | 0.3039 |
| 13 | 0.2635 | 0.3186 | 0.3185 | 0.3175 | 0.3069 | 0.2684 | 0.2996 | 0.3014 |
| 14 | 0.2635 | 0.3216 | 0.3226 | 0.3174 | 0.3066 | 0.2679 | 0.3016 | 0.2999 |

Example 5

Pharmacokinetic Studies

5.1. In Vitro Metabolism Study

Figure 3:
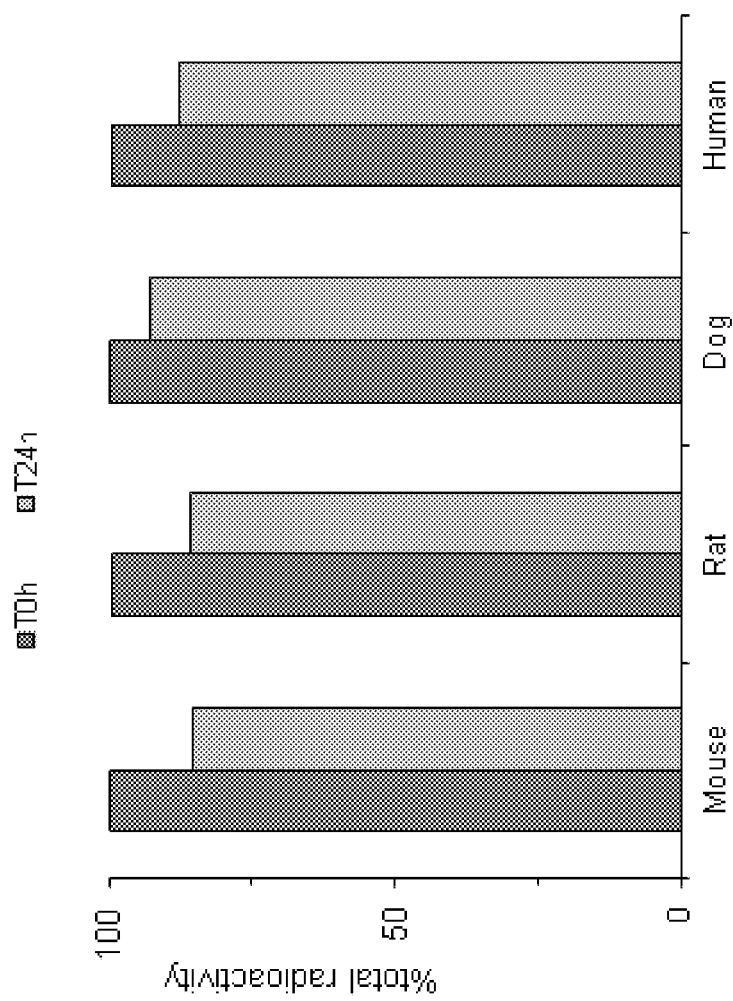
FIG. 3: Shows the in vitro metabolic profile of the compound according to Formula II

A study comparing the metabolism of [$^{14}$C]-compound according to Formula II in hepatocytes of mouse, rat, dog and human, clearly demonstrates that the compound according to Formula II was stable in all species, and confirms that the extent of metabolism was low in all species, with at least 80% of the compound according to Formula II after 24 h, as shown on FIG. 3.

Table IV shows the radiometric metabolic profile of the compound according to Formula II, in human and animal species hepatocytes, which displayed one main metabolite (the compound according to Formula I, 11%) and two minor ones (not characterized, <1.0%, visible on chromatograms).

5.2.1.1.2. Pharmacokinetic Study

The compound according to Formula I was formulated in 0.5% methylcellulose and dosed orally to 3 or 6 animals as a single esophageal gavage at dose ranging from 15 to 180 mg/kg under a dosing volume of 5 or 10 mL/kg.

The compound according to Formula II was formulated in 0.5% methylcellulose and dosed orally to 3 animals (or 3 mouse/time points) as a single esophageal gavage at dose ranging from 15 to 45 mg/kg under a dosing volume of 5 or 10 mL/kg.

Blood samples were collected over a 24-h period via the jugular vein (dog, minipig), ear blood vessel (rabbit), cardiac puncture (mouse) or retro-orbital sinus (rat) with lithium heparin as anti-coagulant. Whole blood samples were centrifuged and the resulting plasma samples were stored at −20° C. pending analysis.

TABLE IV

In vitro metabolic profile of the compound according to Formula II

| Structure | | | Metabolite2 | Metabolite3 |
|---|---|---|---|---|
| Mouse | 85% | 14% | <1.0% | <1.0% |
| Rat | 86% | 12% | <1.0% | <1.0% |
| Dog | 93% | 5.7% | <1.0% | 1.0% |
| Human | 88% | 11.2% | <1.0% | <1.0% |

5.2. In Vivo Studies

5.2.1. Single Dose Pharmacokinetics in Animals

Pharmacokinetic studies were performed in various animal species dosed with the compound according to Formula II to determine the exposure to the compound according to Formula I as well as its apparent terminal half life ($T_{1/2}$), when possible.

5.2.1.1. Protocol

5.2.1.1.1. Animals

Sprague-Dawley rats (male, 200-250 g), CD1 mice (male, 25-30 g), Beagle dogs (male, 9-10 kg), Göttingen minipigs (male, 10-15 kg) and New Zealand White rabbits (male, 3-5 kg) were acclimatized for at least 7 days before treatment and were kept on a 12 hr light/dark cycle (07h00-19h00).

Temperature was maintained at approximately 22° C., and food and water were provided ad libitum.

5.2.1.1.3. Quantification of Compound Levels in Plasma

Plasma concentrations of the compound according to Formula I and of the compound according to Formula II were determined by an LC-MS/MS method with a limit of quantification ≤10.0 ng/mL for both Formula I and Formula II for all species.

5.2.1.1.4. Determination of Pharmacokinetic Parameters

Pharmacokinetic parameters were calculated using a statistical analysis package (WinNonLin (Pharsight, Sunnyvale, Calif.: CA 94086, USA).

5.2.1.2. Results

5.2.1.2.1. Result Upon Administration of the Compound According to Formula I Alone Using the protocol described above, the AUC and apparent terminal half life were determined as shown below in Table V.

TABLE V

Exposure and apparent terminal half life in various species upon administration of the compound of the invention according to Formula I.

| Species | Dose (mg/kg) | AUC (μg · h/mL) | Apparent terminal half life (h) |
|---|---|---|---|
| Rat | 20 | 19.7 (Male) | 7 |
| | | 25.2 (Female) | |
| | 60 | 102 (Male) | |
| | | 123 (Female) | |
| | 180 | 376 (Male) | |
| | | 541 (Female) | |
| Dog (Male) | 10 | 49.4 | 9 |
| | 25 | 114 | |
| | 50 | 290 | |
| Rabbit (Female) | 125 | 777 | Not Determined |
| | 250 | 1029 | |

The results presented in Table V show that the compound according to Formula I when dosed on its own is readily absorbed, and thus is exposed in vivo.

5.2.1.2.2. Result Upon Administration of the Compound According to Formula II Alone Upon administration of the compound according to Formula II, the apparent terminal elimination half-life of the compound according to Formula I was determined in mouse (2.1 h) and rabbit (4.6 h).

5.2.2. Single Dose Pharmacokinetics in Human

5.2.2.1. Protocol

Subjects received the single dose (10, 25, 50, 100, or 200 mg) of the compound according to Formula II as capsules after a high-fat high-calorie breakfast (FDA recommendation: a high-fat (approximately 50 percent of total caloric content of the meal), and high-calorie (approximately 800 to 1000 calories). An example test meal would be two eggs fried in butter, two strips of bacon, two slices of toast with butter, four ounces of hash brown potatoes and eight ounces of whole milk. Substitutions in this test meal can be made as long as the meal provides a similar amount of calories from protein, carbohydrate, and fat and has comparable meal volume and viscosity.

Serial blood samples were collected over 72 h to determine plasma concentrations of the compounds according to Formula II and Formula I using a validated liquid chromatography-mass spectrometry/mass spectrometry (LC-MS/MS) method with a limit of quantification of 1.00 ng/mL. PK parameters were assessed using a statistical analysis package (WinNonLin (Pharsight, Sunnyvale, Calif.: CA 94086, USA).

5.2.2.2. Plasma Elimination Results

Mean plasma concentration-time profiles of the compound according to Formula II and the compound according to Formula I were measured.

Elimination of the compound according to Formula II over time displayed a biphasic profile with a mean apparent terminal elimination half-life of about 5-8 h.

In contrast, the plasma elimination of the compound according to Formula I displayed a monophasic profile with a mean apparent terminal elimination half-life of ranging from 21 to 27 h.

5.2.2.3. Exposure to the Compound According to Formula II and Formula I

In order to show the comparative exposures of the two compounds, the AUC of the compounds according to Formula I and the compound according to Formula II were calculated. The AUC value represents the total exposure of the compound in the species after dosing. These values were then expressed as a ratio of AUC of the compound according to Formula I: AUC of the compound according to Formula II in FIG. 4. From this ratio it can clearly be seen that there was a significant difference in exposure to a compound according to Formula I after administration of a compound according to Formula II in human compared to the exposure seen in animals for therapeutically equivalent doses. Without wanting to be bound by theory, it was believed that this difference was related to the difference in the apparent terminal half-life in the different species.

TABLE VI

Ratio of exposure (expressed as AUC) for [Formula I]:[Formula II] measured on administration of the compound according to Formula II.

| Species | Formula I | Formula II | Ratio I/II |
|---|---|---|---|
| Mouse (30 mg/kg) | 11.4 | 7.3 | 1.56 |
| Rat (45 mg/kg) | 13.3 | 33.3 | 0.40 |
| Dog (15 mg/kg) | 10.6 | 44.9 | 0.24 |
| Minipig (30 mg/kg) | 16.7 | 19.1 | 0.88 |
| Rabbit (20 mg/kg) | 10 | 26 | 0.38 |
| Human (10 mg) | 2.89 | 0.128 | 22.58 |
| Human (25 mg) | 7.22 | 0.331 | 21.81 |
| Human (50 mg) | 14.6 | 0.735 | 19.86 |
| Human (100 mg) | 26.9 | 1.69 | 15.92 |
| Human (200 mg) | 57.6 | 4.5 | 12.8 |

5.2.3. Repeated Dose Pharmacokinetics in Human

5.2.3.1. Protocol

Subjects received repeated dose (25, 50 and 100 mg BID or 200, 300 and 450 mg QD) of the compound according to Formula II as capsules after a standard breakfast for 10 days.

Serial blood samples were collected over 12 h (BID regimen) or 24 h (QD regimen) on day 1 and 10 to determine plasma concentrations of the compounds according to Formula II and Formula I using a validated liquid chromatography-mass spectrometry/mass spectrometry (LC-MS/MS) method with a limit of quantification of 1.00 ng/mL for both Formula. PK parameters were assessed using a statistical analysis package (WinNonLin (Pharsight, Sunnyvale, Calif.: CA 94086, USA).

5.2.3.2. Plasma Elimination Results

Mean plasma concentration-time profiles of the compound according to Formula II and the compound according to Formula I were measured.

Elimination of the compound according to Formula II over time displayed a biphasic profile with a mean apparent terminal elimination half-life of about 4-11 h.

In contrast, the plasma elimination of the compound according to Formula I displayed a monophasic profile with a mean apparent terminal elimination half-life of ranging from 22 to 27 h.

5.2.3.3. Exposure to the Compound According to Formula II and Formula I

In order to show the comparative exposures of the two compounds, the AUC of the compounds according to Formula I and the compound according to Formula II were calculated. The AUC value represents the steady state exposure of the compounds after repeated dosing. The ratio of AUC of the compound according to Formula I: AUC of the compound according to Formula II is display in Table VTT.

TABLE VII

Exposure (expressed as AUC in µg · h/mL) for Formula II and Formula I measured on repeated administration of the compound according to Formula II.

| | Regimen | | | | |
|---|---|---|---|---|---|
| | BID | | | QD | |
| Dose | 25 mg | 50 mg | 100 mg | 200 mg | 300 mg | 450 mg |
| Formula II | 0.346 | 0.758 | 2.38 | 4.45 | 4.40 | 10.2 |
| Formula I | 8.66 | 15.2 | 41.1 | 70.0 | 66.1 | 102 |
| Ratio I/II | 24.4 | 20.5 | 18.3 | 16.1 | 15.0 | 10.1 |

5.2.4. Conclusion

The compound according to Formula I displays a very similar profile in all species in vitro. However, unexpectedly, in vivo, this profile was very different between human and the other animal species, where the apparent terminal half life was at least 3 times higher in human. This longer apparent terminal half-life results in accumulation of the compound according to Formula I in human which offers the possibility of a wide range of dosage regimen frequency, in particular low frequency dosage regimen, and more particularly from once daily to once every two weeks, most particularly from once daily to once weekly.

5.3. Target Inhibition

The compound according to Formula II was dosed daily in healthy volunteers at 200 mg QD and 100 mg BID.

Figure 5:
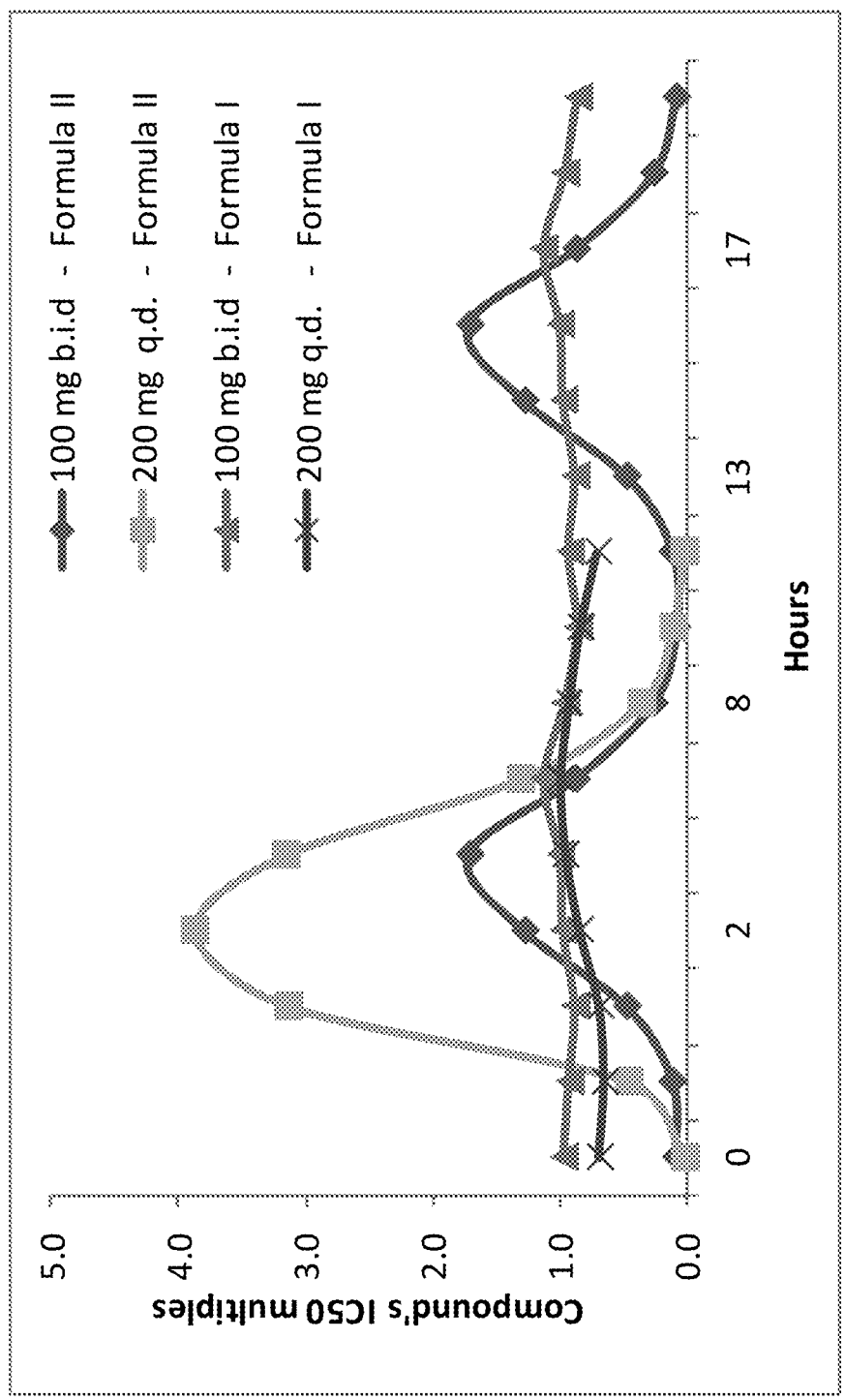
FIG. 5: Shows the values for the exposure levels of the disclosed compounds after administration of the compound according to Formula II expressed as a multiple of the $IC_{50}$ value.

The resulting levels of Formula II and Formula I were then measured and plotted (FIG. 5) as multiples of their respective $IC_{50}$ as determined by the Whole Blood assay described above in Example 3.4.

Figure 4:
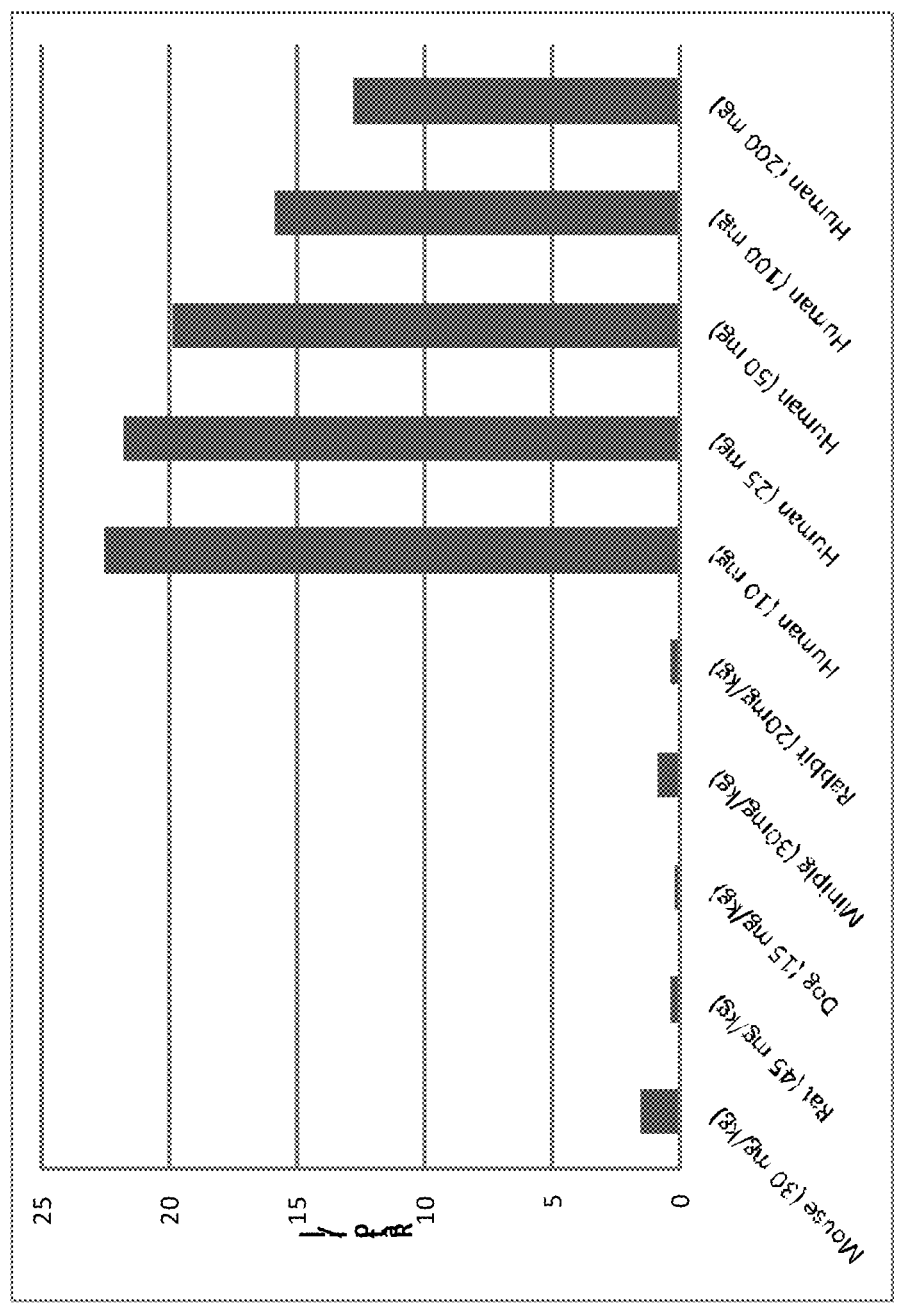
FIG. 4: Shows the ratio of exposure (expressed as AUC) for Formula I:Formula II measured on administration of the compound according to Formula II.
Figure 6:
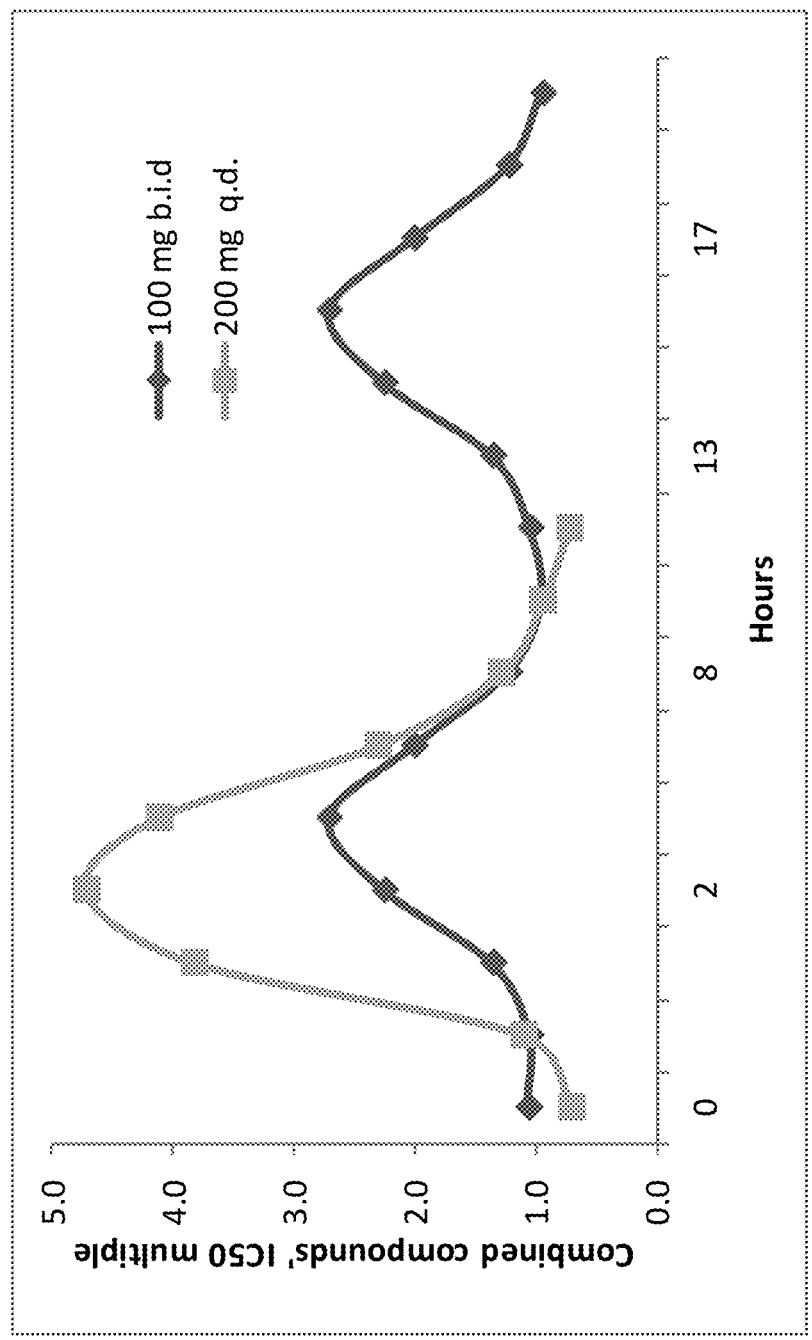
FIG. 6: Shows the combined values for the exposure levels over a 24 h period of the compounds according to Formula I and Formula II after administration of the compound according to Formula II expressed as a multiple of the $IC_{50}$ value.

Both Formula II and Formula I were active alone in the CIA rat model. Surprisingly, as shown in FIG. 4, the administration of compound Formula II is associated with 2 active species, Formula I and Formula II. Without wishing to be bound by theory, it is believed that Formula II provides rapid inhibition of the target, and the compound according to Formula I is then steadily formed and accumulated, thus resulting in a drug level above the $IC_{50}$ level over almost 24 h as shown in the cumulative fold over $IC_{50}$ on FIG. 6. This was particularly unexpected, as no such profile could have been predicted from the model in rat, mouse and rabbit, where such accumulation does not occur.

TABLE VIII

Ratio calculated as [blood circulating dose of the compounds expressed as ng/mL]/[circulating dose of the same compounds at $IC_{50}$ quantity].

| Time | Formula II at 100 mg BID | | | Formula II at 200 mg QD | | |
|---|---|---|---|---|---|---|
| point (h) | Formula II | Formula I | Formula I + Formula II | Formula II | Formula I | Formula I + Formula II |
| 0 | 0.09 | 0.97 | 1.06 | 0.02 | 0.69 | 0.71 |
| 0.5 | 0.12 | 0.93 | 1.04 | 0.46 | 0.65 | 1.11 |
| 1 | 0.48 | 0.88 | 1.36 | 3.14 | 0.69 | 3.83 |
| 2 | 1.28 | 0.97 | 2.25 | 3.88 | 0.84 | 4.72 |
| 3 | 1.71 | 1.00 | 2.71 | 3.16 | 0.96 | 4.12 |
| 5 | 0.88 | 1.13 | 2.01 | 1.31 | 1.00 | 2.31 |
| 8 | 0.26 | 0.96 | 1.22 | 0.36 | 0.93 | 1.29 |
| 12 | 0.09 | 0.86 | 0.94 | — | — | — |
| 12.5 | 0.12 | 0.93 | 1.04 | — | — | — |
| 13 | 0.48 | 0.88 | 1.36 | — | — | — |
| 14 | 1.28 | 0.97 | 2.25 | — | — | — |
| 15 | 1.71 | 1.00 | 2.71 | — | — | — |
| 17 | 0.88 | 1.13 | 2.01 | — | — | — |
| 20 | 0.26 | 0.96 | 1.22 | — | — | — |
| 24 | 0.09 | 0.86 | 0.94 | 0.11 | 0.84 | 0.95 |

General Conclusions

The data provided in the present application demonstrate that although the compound according to Formula I exhibits similar in vitro potency against JAK1 and JAK2 in a biochemical assay, the in vitro whole blood selectivity assay, closer to physiological conditions (Saharinen et al. 2000 Mol. Cell. Biol., 20(10), 3387), shows that the compound of the invention according to Formula I exhibits over 10 fold selectivity for JAK1 over JAK2. Furthermore, the compound of the invention according to Formula I shows an unexpected in vivo profile in human compared to what could have been anticipated from the in vitro data or from in vivo data in other species. In particular, the compound according to Formula I displays a significantly longer apparent terminal half life in human ranging from 21 to 27 h that could not have been predicted by a person of skill in the art, which may result in advantages ranging from low frequency dosage regimen and increased patient compliance. In particular, the impact of non adherence if the patient misses a dose, might be reduced.

Example 6

Additional Protocols

6.1. Thermodynamic Solubility

A solution of 1 mg/mL of the test compound is prepared in a 0.2M phosphate buffer pH 7.4 or a 0.1M citrate buffer pH 3.0 at room temperature in a glass vial.

The samples are rotated in a Rotator drive STR 4 (Stuart Scientific, Bibby) at speed 3.0 at room temperature for 24 h.

After 24 hrs, 800 µL of the sample is transferred to an eppendorf tube and centrifuged 5 min at 14000 rpm. 200 µL of the supernatant of the sample is then transferred to a MultiscreenR Solubility Plate (Millipore, MSSLBPC50) and the supernatant is filtered (10-12" Hg) with the aid of a vacuum manifold into a clean Greiner polypropylene V-bottom 96 well plate (Cat no. 651201). 5 µL of the filtrate is diluted into 95 µL (F20) of the same buffer used to incubate in the plate containing the standard curve (Greiner, Cat no. 651201).

The standard curve for the compound is prepared freshly in DMSO starting from a 10 mM DMSO stock solution diluted factor 2 in DMSO (5000 µM) and then further diluted in DMSO up to 19.5 µM. 3 µL of the dilution series as from 5000 µM is then transferred to a 97 µL acetonitrile-buffer mixture (50/50). The final concentration range is 2.5 to 150 µM.

The plate is sealed with sealing mats (MA96RD-045, Kinesis, Cambs, PE19 8YX, UK) and samples are measured at room temperature on LCMS (ZQ 1525 from Waters) under optimized conditions using Quanoptimize to determine the appropriate mass of the molecule.

The samples are analyzed on LCMS with a flow rate of 1 mL/min. Solvent A is 15 mM ammonia and solvent B is acetonitrile. The sample is run under positive ion spray on an XBridge $C_{18}$ 3.5 µM (2.1×30 mm) column, from Waters. The solvent gradient has a total run time of 2 min and ranges from 5% B to 95% B.

Peak areas are analyzed with the aid of Masslynx software package and peak areas of the samples are plotted against the standard curve to obtain the solubility of the compound.

Solubility values are reported in µM or µg/mL.

6.2. Aqueous Solubility

6.2.1. Aqueous Solubility 2% DMSO Procedure

Starting from a 10 mM stock in DMSO, a serial dilution of the compound is prepared in DMSO. The dilution series is transferred to a 96 NUNC Maxisorb plate F-bottom (Cat no. 442404) and 0.2M phosphate buffer pH7.4 or 0.1M citrate buffer pH 3.0 at room temperature is added.

The final concentration ranges from 200 µM to 2.5 µM in 5 equal dilution steps. The final DMSO concentration does not exceed 2%. 200 µM Pyrene is added to the corner points of each 96 well plate and serves as a reference point for calibration of Z-axis on the microscope.

The assay plates are sealed and incubated for 1 hr at 37° C. while shaking at 230 rpm. The plates are then scanned under a white light microscope, yielding individual pictures of the precipitate per concentration. The precipitate is analyzed and converted into a number which is plotted onto a graph. The first concentration at which the compound appears completely dissolved is the concentration that is reported below, however the true concentration will lie somewhere between this concentration and one dilution step higher.

Solubility values measured according to this protocol are reported in µg/mL.

6.2.2. Aqueous Solubility 3% DMSO Procedure

Starting from a 10 mM stock in DMSO, a serial dilution of the compound is prepared in DMSO. The dilution series is transferred to a 96 NUNC Maxisorb plate F-bottom (Cat no. 442404) and 0.1M phosphate buffer pH7.4 or 0.1M citrate buffer pH3.0 at room temperature is added.

The final concentration will range from 300 µM to 18.75 µM in 5 equal dilution steps. The final DMSO concentration does not exceed 3%. 200 µM Pyrene is added to the corner points of each 96 well plate and serves as a reference point for calibration of Z-axis on the microscope.

The assay plates are sealed and incubated for 1 h at 37° C. while shaking at 230 rpm. The plates are then scanned under a white light microscope, yielding individual pictures of the precipitate per concentration. The precipitate is analyzed and converted into a number with a software tool which can be plotted onto a graph. The first concentration at which the compound appears completely dissolved is the concentration reported; however the true concentration lies somewhere between this concentration and one dilution step higher.

Solubility values measured according to this protocol are reported in µg/mL.

6.3. Plasma Protein Binding (Equilibrium Dialysis)

A 10 mM stock solution of the compound in DMSO is diluted with a factor 5 in DMSO. This solution is further diluted in freshly thawed human, rat, mouse or dog plasma (BioReclamation INC) with a final concentration of 10 µM and final DMSO concentration of 0.5% (5.5 µL in 1094.5 µL plasma in a PP-Masterblock 96 well (Greiner, Cat no. 780285))

A Pierce Red Device plate with inserts (ThermoScientific, Cat no. 89809) is prepared and filled with 750 µL PBS in the buffer chamber and 500 µL of the spiked plasma in the plasma chamber. The plate is incubated for 4 h at 37° C. while shaking at 230 rpm. After incubation, 120 µL of both chambers is transferred to 360 µL acetonitrile in a 96-well round bottom, PP deep-well plates (Nunc, Cat no. 278743) and sealed with an aluminum foil lid. The samples are mixed and placed on ice for 30 min. This plate is then centrifuged 30 min at 1200 rcf at 4° C. and the supernatant is transferred to a 96 v-bottom PP plate (Greiner, 651201) for analysis on LCMS.

The plate is sealed with sealing mats (MA96RD-04S) of Kinesis, Cambs, PE19 8YX, UK and samples are measured at room temperature on LCMS (ZQ 1525 from Waters) under optimized conditions using Quanoptimize to determine the appropriate mass of the molecule.

The samples are analyzed on LCMS with a flow rate of 1 mL/min. Solvent A is 15 mM ammonia and solvent B is acetonitrile. The sample is run under positive ion spray on an XBridge $C_{18}$ 3.5 µM (2.1×30 mm) column, from Waters. The solvent gradient has a total run time of 2 min and ranges from 5% B to 95% B.

Peak area from the compound in the buffer chamber and the plasma chamber are considered to be 100% compound. The percentage bound to plasma is derived from these results and is reported as percentage bound to plasma.

The solubility of the compound in the final test concentration in PBS is inspected by microscope to indicate whether precipitation is observed or not.

6.4. Microsomal Stability

6.4.1. Microsomal Stability 1 h Incubation Procedure

A 10 mM stock solution of compound in DMSO is diluted 1000 fold in a 182 mM phosphate buffer pH7.4 in a 96 deep well plate (Greiner, Cat no. 780285) and pre-incubated at 37° C.

40 µL of deionised water is added to a well of a polypropylene Matrix 2D barcode labelled storage tube (Thermo Scientific) and pre-incubated at 37° C.

A Glucose-6-phosphate-dehydrogenase (G6PDH) working stock solution is prepared in 182 mM phosphate buffer pH7.4 and placed on ice before use. A co-factor containing $MgCl_2$, glucose-6-phosphate and NADP+ is prepared in deionised water and placed on ice before use.

A final working solution containing liver microsomes (Xenotech) of a species of interest (human, mouse, rat, dog), previously described G6PDH and co-factors is prepared and this mix is incubated for no longer than 20 min at room temperature.

30 µL of the pre-heated compound dilution is added to 40 µL of pre-heated water in the Matrix tubes and 30 µL of the microsomal mix is added. Final reaction concentrations are 3

µM compound, 1 mg microsomes, 0.4 U/mL GDPDH, 3.3 mM MgCl$_2$, 3.3 mM glucose-6-phosphate and 1.3 mM NADP+.

To measure the percentage remaining of compound at time zero, MeOH or MeCN is added (1:1) to the well before adding the microsomal mix. The plates are sealed with Matrix Sepra seals (Matrix, Cat. No. 4464) and shaken for a few seconds ensure complete mixing of all components.

The samples which are not stopped are incubated at 37° C., 300 rpm and after 1 hr of incubation the reaction is stopped with MeOH or MeCN (1:1).

After stopping the reaction the samples are mixed and placed on ice for 30 min to precipitate the proteins. The plates are then centrifuged 30 min at 1200 rcf at 4° C. and the supernatant is transferred to a 96 v-bottom PP plate (Greiner, 651201) for analysis on LCMS.

These plates are sealed with sealing mats (MA96RD-04S) of Kinesis, Cambs, PE19 8YX, UK and samples are measured at room temperature on LCMS (ZQ 1525 from Waters) under optimized conditions using Quanoptimize to determine the appropriate mass of the parent molecule.

The samples are analyzed on LCMS with a flow rate of 1 mL/min. Solvent A is 15 mM ammonia and solvent B is methanol or acetonitrile, depending on the stop solution used. The samples are run under positive ion spray on an XBridge C$_{18}$ 3.5 µM (2.1×30 mm) column, from Waters. The solvent gradient has a total run time of 2 min and ranges from 5% B to 95% B.

Peak area from the parent compound at time 0 is considered to be 100% remaining. The percentage remaining after 1 hr incubation is calculated from time 0 and is calculated as the percentage remaining. The solubility of the compound in the final test concentration in buffer is inspected by microscope and results are reported.

The data on microsomal stability are expressed as a percentage of the total amount of compound remaining after 60 min.

6.4.2. Microsomal Stability 30 Min Incubation Procedure

A 10 mM stock solution of compound in DMSO is diluted to 6 µM in a 105 mM phosphate buffer, pH 7.4 in a 96 deep well plate (Greiner, Cat no. 780285) and pre-warmed at 37° C.

A Glucose-6-phosphate-dehydrogenase (G6PDH, Roche, 10127671001) working stock solution of 700 U/mL is diluted with a factor 1:700 in a 105 mM phosphate buffer, pH7.4. A co-factor mix containing 0.528M MgCl$_2$.6H$_2$O (Sigma, M2670), 0.528M glucose-6-phosphate (Sigma, G-7879) and 0.208M NADP+ (Sigma, N-0505) is diluted with a factor 1:8 in a 105 mM phosphate buffer, pH7.4.

A working solution is made containing 1 mg/mL liver microsomes (Provider, Xenotech) of the species of interest (human, mouse, rat, dog, . . . ), 0.8 U/mL G6PDH and co-factor mix (6.6 mM MgCl2, 6.6 mM glucose-6-phosphate, 2.6 mM NADP+). This mix is pre-incubated for 15 min, but never more than 20 min, at room temperature.

After pre-incubation, compound dilution and the mix containing the microsomes, are added together in equal amount and incubated for 30 min at 300 rpm. For the time point of 0 min, two volumes of methanol are added to the compound dilution before the microsome mix is added. The final concentration during incubation are: 3 µM test compound or control compound, 0.5 mg/mL microsomes, 0.4 U/mL G6PDH, 3.3 mM MgCl$_2$, 3.3 mM glucose-6-phosphate and 1.3 mM NaDP+.

After 30 min of incubation, the reaction is stopped with 2 volumes of methanol.

Of both time points, samples are mixed, centrifuged and the supernatant is harvested for analysis on LC-MS/MS. The instrument responses (i.e. peak heights) are referenced to the zero time-point samples (as 100%) in order to determine the percentage of compound remaining Standard compounds Propanolol and Verapamil are included in the assay design.

The data on microsomal stability are expressed as a percentage of the total amount of compound remaining after 30 min.

Hepatocyte stability (Concentrations of the compound according to Formula II and its main metabolites (as % of total radioactivity) after 24 h incubation of 100 µM [$^{14}$C]-Compound according to Formula II in hepatocyte suspension of different species)

6.5. Caco2 Permeability

Bi-directional Caco-2 assays are performed as described below. Caco-2 cells are obtained from European Collection of Cell Cultures (ECACC, cat 86010202) and used after a 21 day cell culture in 24-well Transwell plates (Fisher TKT-545-020B).

2×10$^5$ cells/well are seeded in plating medium consisting of DMEM+GlutaMAXI+1% NEAA+10% FBS (FetalClone II)+1% Pen/Strep. The medium is changed every 2-3 days.

Test and reference compounds (propranolol and rhodamine-123 or vinblastine, all purchased from Sigma) are prepared in Hanks' Balanced Salt Solution containing 25 mM HEPES (pH7.4) and added to either the apical (125 µL) or basolateral (600 µL) chambers of the Transwell plate assembly at a concentration of 10 µM with a final DMSO concentration of 0.25%.

50 µM Lucifer Yellow (Sigma) is added to the donor buffer in all wells to assess integrity of the cell layers by monitoring Lucifer Yellow permeation. As Lucifer Yellow (LY) cannot freely permeate lipophilic barriers, a high degree of LY transport indicates poor integrity of the cell layer.

After a 1 hr incubation at 37° C. while shaking at an orbital shaker at 150 rpm, 70 µL aliquots are taken from both apical (A) and basal (B) chambers and added to 100 µL 50:50 acetonitrile:water solution containing analytical internal standard (0.5 µM carbamazepine) in a 96 well plate.

Lucifer yellow is measured with a Spectramax Gemini XS (Ex 426 nm and Em 538 nm) in a clean 96 well plate containing 150 µL of liquid from basolateral and apical side.

Concentrations of compound in the samples are measured by high performance liquid-chromatography/mass spectroscopy (LC-MS/MS).

Apparent permeability (Papp) values are calculated from the relationship:

$$Papp=[compound]acceptor\ final \times Vacceptor/([compound]donor\ initial \times Vdonor)/Tinc \times Vdonor/surface\ area \times 60 \times 10^{-6}\ cm/s$$

V=chamber volume

Tinc=incubation time.

Surface area=0.33 cm$^2$

The Efflux ratios, as an indication of active efflux from the apical cell surface, are calculated using the ratio of Papp B>A/Papp A>B.

The following assay acceptance criteria are used:
Propranolol: Papp (A>B) value ≥20($\times 10^{-6}$ cm/s)
Rhodamine 123 or Vinblastine: Papp (A>B) value <5 ($\times 10^{-6}$ cm/s) with Efflux ratio ≥5.
Lucifer yellow permeability: ≤100 nm/s

6.6. Septic Shock Model

Injection of lipopolysaccharide (LPS) induces a rapid release of soluble tumour necrosis factor (TNF-alpha) into the periphery. This model is used to analyse prospective blockers of TNF release in vivo.

Six BALB/cJ female mice (20 g) per group are treated at the intended dosing once, po. Thirty min later, LPS (15 µg/kg; E. Coli serotype 0111:B4) is injected ip. Ninety min later, mice are euthanized and blood is collected. Circulating TNF alpha levels are determined using commercially available ELISA kits. Dexamethasone (5 µg/kg) is used as a reference anti-inflammatory compound.

6.7. MAB Model

The MAB model allows a rapid assessment of the modulation of an RA-like inflammatory response by therapeutics (Khachigian L M. Nature Protocols (2006) 2512-2516: Collagen antibody-induced arthritis). DBA/J mice are injected i.v. with a cocktail of mAbs directed against collagen II. One day later, compound treatment is initiated (vehicle: 10% (v/v) HPβCD). Three days later, mice receive an i.p. LPS injection (50 µg/mouse), resulting in a fast onset of inflammation. Compound treatment is continued until 10 days after the mAb injection. Inflammation is read by measuring paw swelling and recording the clinical score of each paw. The cumulative clinical arthritis score of four limbs is presented to show the severity of inflammation. A scoring system is applied to each limb using a scale of 0-4, with 4 being the most severe inflammation.
  0 Symptom free
  1 Mild, but definite redness and swelling of one type of joint such as the ankle or wrist, or apparent redness and swelling limited to individual digits, regardless of the number of affected digits
  2 Moderate redness and swelling of two or more types of joints
  3 Severe redness and swelling of the entire paw including digits
  4 Maximally inflamed limb with involvement of multiple joints

6.8. Oncology Models

In vivo models to validate efficacy of small molecules towards JAK2-driven myeloproliferative diseases are described by Wernig et al. Cancer Cell 13, 311, 2008 and Geron et al. Cancer Cell 13, 321, 2008.

6.9. Mouse IBD Model

In vitro and in vivo models to validate efficacy of small molecules towards IBD are described by Wirtz et al. 2007.

6.10. Mouse Asthma Model

In vitro and in vivo models to validate efficacy of small molecules towards asthma are described by Nials et al., 2008; Ip et al. 2006; Pernis et al., 2002; Kudlacz et al., 2008.

FINAL REMARKS

It will be appreciated by those skilled in the art that the foregoing descriptions are exemplary and explanatory in nature, and intended to illustrate the invention and its preferred embodiments. Through routine experimentation, an artisan will recognise apparent modifications and variations that may be made without departing from the spirit of the invention. Thus, the invention is intended to be defined not by the above description, but by the following claims and their equivalents.

All publications, including but not limited to patents and patent applications, cited in this specification are herein incorporated by reference as if each individual publication were specifically and individually indicated to be incorporated by reference herein as though fully set forth.

From the foregoing description, various modifications and changes in the compositions and methods of this invention will occur to those skilled in the art. All such modifications coming within the scope of the appended claims are intended to be included therein.

It should be understood that factors such as the differential cell penetration capacity of the various compounds can contribute to discrepancies between the activity of the compounds in the in vitro biochemical and cellular assays.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

Chemical structures shown herein were prepared using either ChemDraw® or ISIS®/DRAW. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

REFERENCES a) Vainchenker W. et al. 2008 Seminars in Cell & Developmental Biology, 19, 385-393
b) Verstovsek et al. 2009 Hematology Am Soc Hematol Educ Program., 636-42
c) Elie Dolgin et al. 2011 Nature Reviews Drug Discovery, 10, 717-718
d) Smolen et al. 2003 Nat Rev Drug Discov., 2, 473-88
e) Lee D M et al. 2001 Lancet, 358, 903-11
f) Choy E H et al. 2001 N Engl J. Med., 344, 907-16
g) O'Dell J R. 2004 N Engl J. Med., 350(25), 2591-602
h) Firestein G S. 2003 Nature, 423, 356-61
i) Kopf et al. 2010 Nat. Rev. Drug Disc., 703-718
j) Zenz R et al. 2005 Nature, 437 (7057), 369-75
k) Committee for Medicinal Products for Human Use (CHMP) (18 Nov. 2004). "Guideline on Clinical Investigation of Medicinal Products indicated for the treatment of Psoriasis"
l) Punwani et al., 2012 "Preliminary clinical activity of a topical JAK1/2 inhibitor in the treatment of psoriasis" J Am Acad Dermatol., 67, 4, 658-664
m) Zikherman et al. 2011 J Clin Invest. 1(12), 4618-21 n) O'Sullivan et al. 2007 Mol. Immunol. 44(10), 2497-506
o) Xiang et al. 2008 Blood 111-9, 4809-4812
p) Mullighan C G et al. 2009 PNAS 106(23), 9414-9418
q) Zhang et al. 1996 PNAS 93, 9148-9153
r) Constantinescu et al. 2007 Trends in Biochemical Sciences 33(3), 122-131
s) Tam et al. 2007 British Journal of Cancer 97, 378-383
t) Berishaj et al. 2007, Breast Cancer Research 9: R32
u) Naka et al. 2002 Arthritis Res. 4 (suppl 3): 5233-5242
v) Ingersoll et al. 2008 J Behav Med. 31(3), 213-224
w) Bundgard, H., Design of Prodrugs, pp. 7-9, 21-24, Elsevier, Amsterdam 1985
x) Remington's Pharmaceutical Sciences, 17th edition, 1985, Part 8, Mack Publishing Company, Easton, Pa.
y) T. W. Greene and P. G. M. Wuts, Protecting Groups in Organic Synthesis, Second Edition, Wiley, New York, 1991
z) WO 2010/149769
aa) Sims N A et al. 2004 Arthritis Rheum. 50, 2338-2346
bb) Jou et al. 2005 Arthritis Rheum. 52, 339-44
cc) Khachigian, L. M. et al. 2006 Nature Protocols 1, 2512-6
dd) Lin H S et al. 2007 Br J. Pharmacol. 150(7), 862-872
ee) Nishida K et al. 2004 Arthritis Rheum. 10, 3365-76
ff) Shelton D L et al. 2005 Pain 116, 8-16
gg) Argiles J M et al. 1998 Curr Opin Clin Nutr Metab Care 1, 245-51
hh) Rall et al. 2004 Rheumatology 43, 1219-23
ii) Walsmith J et al. 2004) J. Rheumatol. 31, 23-9
jj) Salvemini D et al. 2001 Arthritis Rheum. 44, 2909-21
kk) Bush K A et al. 2002 Arthritis Rheum. 46, 802-5
ll) Oste L et al., ECTC Montreal 2007
mm) Saharinen et al. 2000 Mol. Cell. Biol. 20(10), 3387
nn) Wernig et al. 2008 Cancer Cell 13(4), 311-320
oo) Geron et al. 2008 Cancer Cell 13(4), 321-30
pp) Wirtz et al. 2007 Advanced Drug Delivery Reviews, 2007, 1073-1083
qq) Nials et al. 2008 Disease Models & Mechanisms, 213-220
rr) Ip et al. 2006 Clin. Exp. Immun, 162-172
ss) Pernis et al. 2002 J. Clin. Invest. 1279
tt) Kudlacz et al. 2008 Eur J Pharmaco 154-161
uu) McGinnity et al. Drug Metabolism and Disposition 2004, 32, 11, 1247.

The invention claimed is:

1. A method for the treatment of a mammal afflicted with rheumatoid arthritis, which method comprises administering a therapeutically effective amount of a compound according to Formula I:

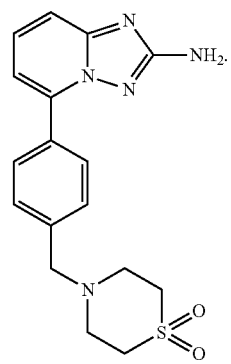

2. The method according to claim 1, wherein the said compound is administered in combination with one or more additional therapeutic agents, wherein said additional therapeutic agent is a rheumatoid arthritis treating agent.

3. The method according to claim 2, wherein the additional therapeutic agent is according to Formula II:

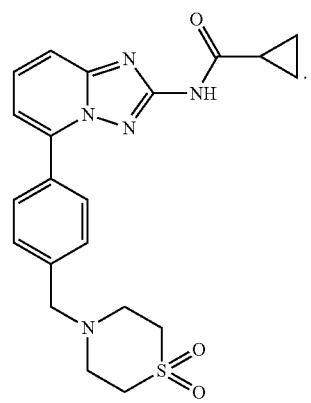

4. The method according to claim 3, wherein the ratio of Formula I/Formula II is from 1/5 to 1/20.

5. The method according to claim 3, wherein the ratio of Formula I/Formula II is from 1/5 to 1/10.

6. The method according to claim 1, wherein the mammal is a human.

* * * * *